United States Patent [19]

Lerner et al.

[11] Patent Number: 5,665,865

[45] Date of Patent: Sep. 9, 1997

[54] METAL BINDING PROTEINS

[75] Inventors: Richard A. Lerner, La Jolla; Victoria A. Roberts, San Diego; Elizabeth D. Getzoff, San Diego; John A. Tainer, San Diego, all of Calif.; Stephen J. Benkovic, State College, Pa.

[73] Assignee: The Scripps Research Institute, La Jolla, Calif.

[21] Appl. No.: 343,658

[22] Filed: Nov. 22, 1994

Related U.S. Application Data

[63] Continuation of Ser. No. 64,795, May 19, 1993, abandoned, which is a continuation of Ser. No. 539,980, Jun. 18, 1990, abandoned, which is a continuation-in-part of Ser. No. 521,258, May 8, 1990, abandoned.

[51] Int. Cl.$^6$ ............... A61K 39/395; C12N 1/21
[52] U.S. Cl. ............... 530/387.3; 424/133.1; 435/69.6; 435/172.3; 435/252.3; 435/252.33
[58] Field of Search ............... 530/387.3; 424/133.1; 435/69.6, 172.3, 252.3, 252.33

[56] References Cited

PUBLICATIONS

Stearns et al. Journal of Biological Chemistry vol. 263 No. 2, 1988 pp. 826–832.
Tao et al. Journal of Immunology 1989 vol. 143 2595–2601.
Burgess et al. Journal of Cell Biology vol. 111 Nov. 1990 2129–2138.
Lazar et al. Molecular and Cellular Biology 1988, 1247–1252.
Getzoff et al., *Adv. Immunol.*, 43:1–98 at p.18 (1989).
Chothia, *Nature*, 342:877–883 (1989).
Bird et al., *Science*, 242:423–426 (1988).
Freeman et al., *Adv. Protein Chem.*, 22:257–424 (1967).
Kannan et al., *Anals. New York Acad. Sci.*, 429:49–60 (1984).
Tainer et al., *J. Mol. Biol.*, 160:181–217 (1982).
Kannan et al., *Proc. Natl. Acad. Sci. USA*, 72:51–55 (1975).
Rees et al., *J. Mol. Biol.*, 168:367–387 (1983).
Tainer et al., *Nature*, 306:284–287 (1983).
Holmes et al., *J. Mol. Biol.*, 160:623–639 (1982).
Pauptit et al., *J. Mol. Biol.*, 199:525–537 (1988).
Brown, et al., *Cancer Res. 50:* 835s–839s (1990).
Brown, et al., *Anal. Biochem. 172:* 22–28 (1988).

*Primary Examiner*—Lila Feisee
*Assistant Examiner*—Julie Reeves
*Attorney, Agent, or Firm*—Thomas Fitting; Emily Holmes

[57] ABSTRACT

The invention describes a metal binding protein capable of forming a coordination complex with a metal cation. The protein contains a sequence of amino acid residues that defines a variable domain of an immunoglobulin light chain having a L1 region and a L3 region, and also contains three contact amino acid residues in the variable domain that participate as ligands for the metal coordination complex.

32 Claims, 9 Drawing Sheets

```
1    M  K  K  T  A  I  A  I  A  V  A  L  A  G  F  A  T  V  A  Q
     ATGAAAAAGACAGTATCGCGATTGCGGTAGCACTGGCACTGGCTGGTTTCGCTACCGTAGCGCAG    60

21   A  D  V  M  T  Q  T  P  L  S  L  P  V  S  L  G  D  Q  A
     GCCGACGTCGTTATGACTCAGACTCCACTCTCCCTGTTAGTCTAGGTCTAGGTGATCAAGCC    120

41   S  I  S  C  R  S  S  Q  S  L  V  H  S  N  G  N  T  Y  L  H
     TCCATCTCTTGCAGATCTAGTCAGAGCCTTGTACACAGTAATGGAAACACCTATTTACAT    180

61   W  L  Q  K  P  G  Q  S  P  K  V  L  I  Y  K  V  S  N  R
     TGGTTACTGCAGAAGCCAGGCCAGTCTCCAAAGGTCCTACAAGTTCCAACCGA    240

81   F  S  G  V  P  D  R  F  S  G  S  G  S  G  T  D  F  T  L  K
     TTTCTGGGGTCCCAGACAGGTTCAGTGGCAGTGGATCAGGGACAGATTCACACTCAAG    300

101  I  S  R  V  E  A  E  D  L  G  V  Y  F  C  H  Q  H  T  H  V
     ATCAGCAGAGTGGAGGCTGAGGACCTGGGAGTTTATTTCTGCCATCAACATACACATGTT    360

121  P  W  T  F  G  G  G  T  K  L  E  I  K  G  S  T  S  G  S  G
     CCGTGGACGTTCGGTGGAGGCACCAAGCTTGAAATCAAAGGTTCTACCTCTGGTTCTGGT    420
```

FIG. 1A

```
141  K   S   E   G   K   G   E   K   L   D   E   T   G   G   G   L   V   Q   P
     AAATCTTCTGAAGGTAAAGGTGAAAAACTGGATGAGACTGGAGGAGGCTTGGTGCAACCT  480

161  G   R   P   M   K   L   S   C   V   A   S   G   F   F   S   D   Y   W   M
     GGGAGGCCCATGAAACTCTCCTGTGTTGCCTCTGGATTCACTTTTAGTGACTACTGGATG  540

181  N   W   V   R   Q   S   P   E   K   G   L   E   W   V   A   Q   I   R   N   K
     AACTGGGTCCGCCAGTCTCCAGAGAAAGGACTGGAGTGGGTAGCACAAATTAGAAACAAA  600

201  P   Y   N   Y   E   T   Y   Y   S   D   S   V   K   G   R   F   T   I   S   R
     CCTTATAATTATGAAACATATTATTCAGATTCTGTGAAAGGCAGATTCACCATCTCAAGA  660

221  D   D   S   K   S   S   V   Y   L   Q   M   N   N   L   R   V   E   D   M   G
     GATGATTCCAAAAGTAGTGTCTACCTGCAAATGAACAACTTAAGAGTTGAAGACATGGGT  720

241  I   Y   Y   C   T   G   S   Y   Y   G   M   D   Y   W   G   Q   G   T   S   V
     ATCTATTACTGTACGGGTTCTTACTATGGTATGGACTACTGGGGTCAAGGAACCTCAGTC  780

261  T   V   S
     ACCGTCTCCTAATAAGGATCCAG  803
```

FIG. 1B

METAL BINDING PROTEINS

CROSS REFERENCE TO A RELATED APPLICATION

This is a continuation of application Ser. No. 08/064,795, filed May 19, 1993 (abandoned), which is a continuation of application Ser. No. 07/539,980, filed Jun. 18, 1990 (abandoned), which is a continuation-in-part of application Ser. No. 07/521,258, filed May 8, 1990 (abandoned), the disclosures of which are incorporated by reference herein.

This invention was made with government support under Contract No. F32 GM 12047 awarded by the National Institutes if Health and Contract No. DIR 8822385 awarded by the National Science Foundation. The government has certain rights in the invention.

TECHNICAL FIELD

The present invention relates to metal binding proteins, particularly to antibody molecules that bind metal cations as metalloantibodies.

BACKGROUND

Metalloproteins as a class are proteins having a metal ion complexed with the protein molecule at the protein's metal binding site. The metal ion contributes to the protein's function by a variety of chemical mechanisms including stabilizing protein structure, facilitating electron transfer in oxidation or reduction reactions, and the like.

The stereochemistry of metal ion complex structure in association with protein has been extensively characterized. Studies of known metalloproteins have resulted in the characterization of many metal ions that participate in metal-protein complexes, which help to identify the nature of the metal-protein complex. Three dimensional structures of metalloproteins based on xray crystallographic data are available for numerous metalloproteins and provide further insight into the nature of the metal-protein complex.

Freeman et al., *Adv. Protein Chem.*, 22:257-424 (1967), has described the preparation of synthetic metal binding sites on polypeptides. Alterations of existing metalloproteins have been reported in which amino acid residues that participate in the metal-protein complex were substituted, resulting in changes in the apoprotein's metal ion specificity and in the binding constant for the metal ion. However no protein structure has been sufficiently characterized to allow reproducible protein engineering to form a metal binding site in a protein to provide the benefits of a metal cofactor to a protein.

BRIEF SUMMARY OF THE INVENTION

It has now been discovered that immunoglobulin molecules contain conserved structural regions adjacent to the antibody combining site which can be reproducibly modified to form a metal binding site. Incorporation of selected amino acid residues into a conserved structural region of the protein's primary amino acid sequence provides the metal ligand contact sites necessary to form a metal binding site on the immunoglobulin molecule, thereby producing a metal binding protein.

Thus, in one embodiment, the present invention contemplates a protein capable of forming a coordination complex with a metal cation, i.e., a metalloprotein. The metalloprotein is characterized by 1) a sequence of amino acid residues that defines a variable domain of an immunoglobulin and 2) three contact amino acid residues in the variable domain that define a metal binding site.

In preferred embodiments, the present invention contemplates a light chain variable region of an immunoglobulin having the three contact amino acid residues that form a metal binding site.

In other preferred embodiments the present invention contemplates a heavy chain variable region of an immunoglobulin having three contact amino acid residues that form a metal binding site.

In preferred embodiments, the metalloprotein is operatively linked to a sequence of amino acid residues forming an immunoglobulin heavy chain variable region to form a metalloantibody. Preferred metalloantibody molecules are Fv, Fab or F(ab')$_2$ molecule that bind Zn(II) and are capable of catalytically cleaving a peptide bond in a site specific (amino acid residue sequence specific) manner.

The metalloproteins of the present invention can be used to partition metal cations in solution by admixing metalloprotein with the metal cation-containing solution. The metal cation-binding reaction admixture thus formed is then maintained for a predetermined time period sufficient for the metalloprotein to bind metal cations and form a complex.

BRIEF DESCRIPTION OF THE DRAWINGS

In the drawings, forming a portion of this disclosure:

FIGS. 1A and 1B illustrate the nucleotide sequence of a DNA that codes for a single chain antigen binding protein having a metal binding site, shown from left to right and in the direction of 5' terminus to 3' terminus using the single letter nucleotide base code. The structural gene for the mature antigen binding protein begins at base 1 and ends at base 789, with the position number of the last base residue in each row indicated to the right of the row showing the sequence.

The amino acid for the single chain antigen binding protein is indicated by the single letter code above the nucleotide base sequence, with the position number for the first residue in each row indicated to the left of the row showing the amino acid residue sequence. The reading frame is indicated by placement of the deduced amino acid residue sequence above the nucleotide sequence such that the single letter that represents each amino acid is located above the middle base in the corresponding codon. The mature antigen binding protein amino acid residue sequence begins at residue 1 and ends at residue 263.

Figure 2:
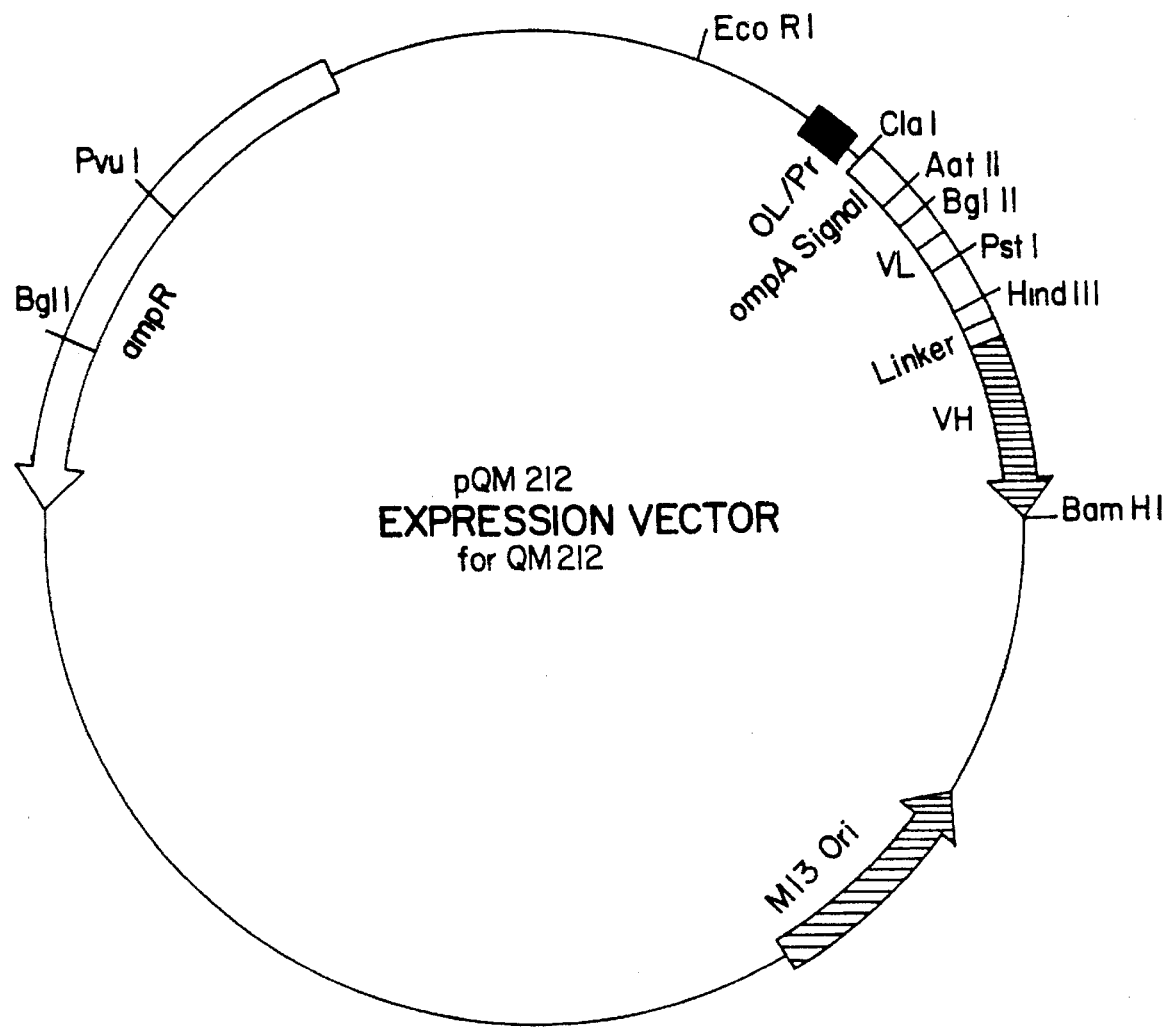

FIG. 2 illustrates the plasmid expression vector pQM212 which contains a structural gene that encodes the amino acid residue sequence shown in FIG. 1 for the antigen binding protein QM212 and has the capacity to direct the expression of QM212. The vector also contains an ampicillin resistance gene (ampR), and M13 origin of replication (M13 Ori), and a lambda promoter (OL/PR) which provides a binding site for the temperature sensitive lambda repressor for expressing the QM212 gene.

Figure 3:
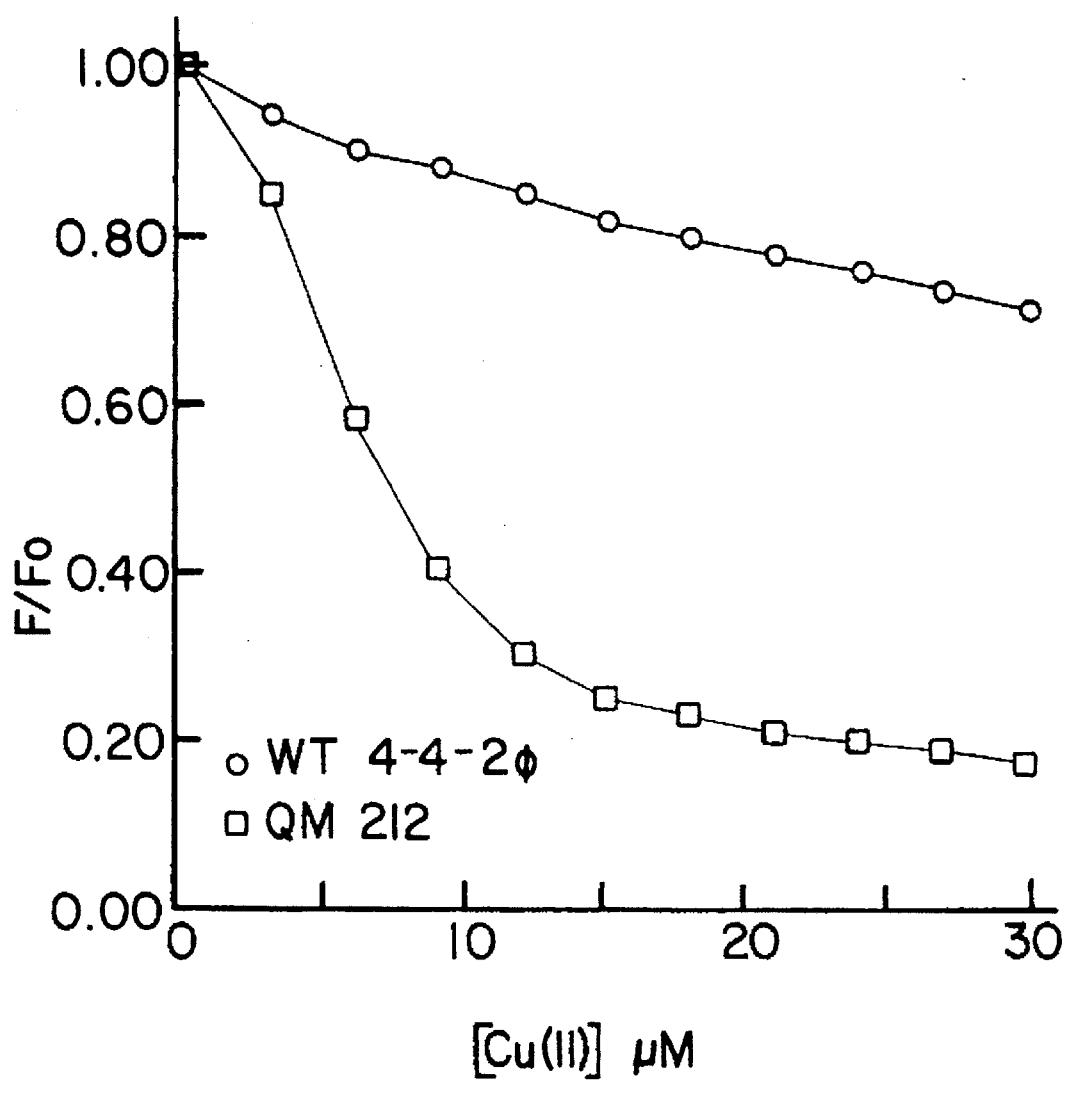

FIG. 3 illustrates the ability of Cu(II) to quench the fluorescence of tryptophan residues present in the QM212 protein solution. The data also illustrate that Cu(II) does not substantially quench fluorescence associated with 4-4-20/212 protein. Fluorescence quenching is expressed as a ratio F/Fo, where 1.0 is an arbitrary unit of 0% quenching in the solution having no added metal (Fo) and F is the emission measured when metal is added. The data show that Cu(II) fluorescence quenching of QM212 displays saturation behavior above about 12–15 μM Cu(II) with an apparent binding constant of $2 \times 10^5 M^{-1}$.

Figure 4A:
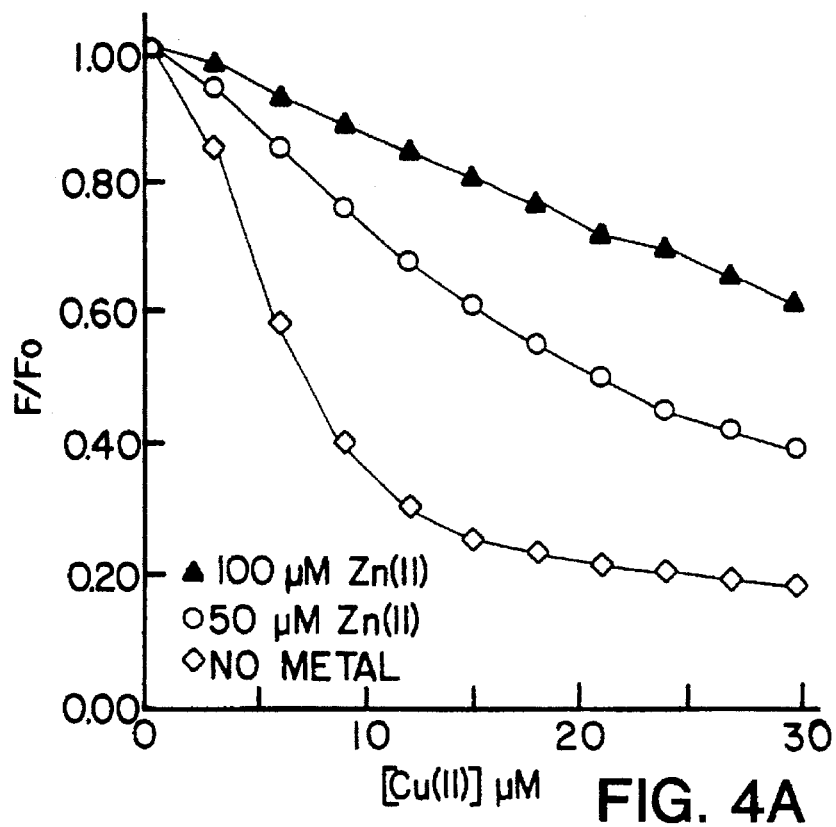
Figure 4B:
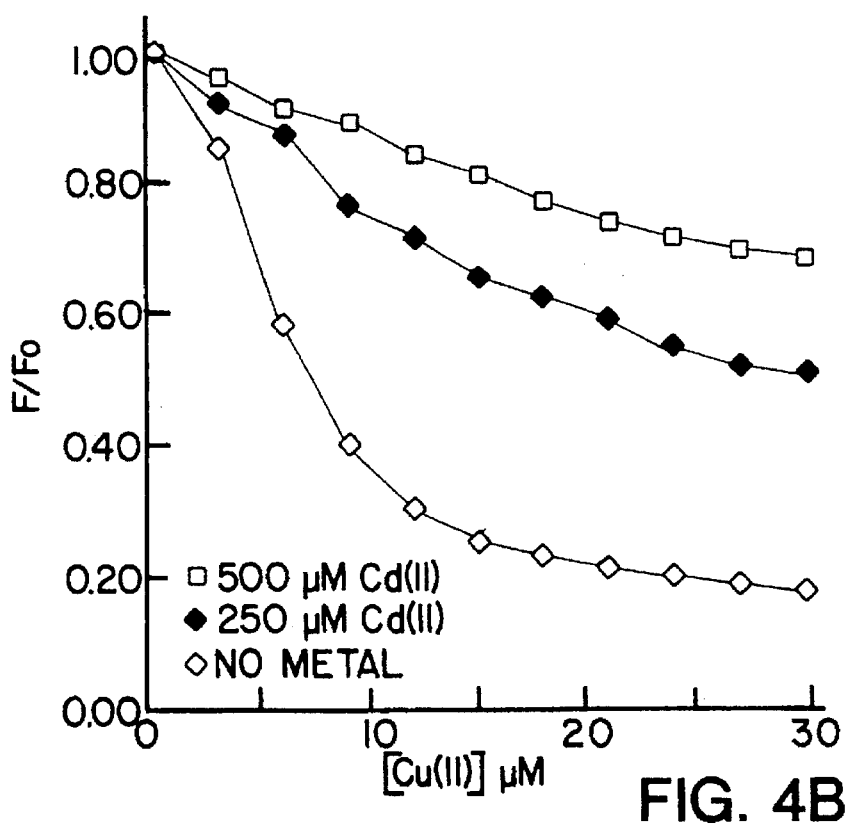

FIGS. 4A and 4B illustrate inhibition of Cu(II) binding to QM212 using the competing metal ions, zinc as Zn(II) (FIG.

4a) and cadmium as Cd(II) (FIG. 4b). Fluorescence quenching is expressed as described in the legend to FIG. 3. Prior to adding Cu(II) to the quenching admixture, various concentrations of Zn(II) or Cd(II) were added to the admixture. The data show that both zinc and cadmium bind QM212 in a dose dependent manner sufficiently to block Cu(II) and inhibit Cu(II) binding to QM212.

Figure 5:
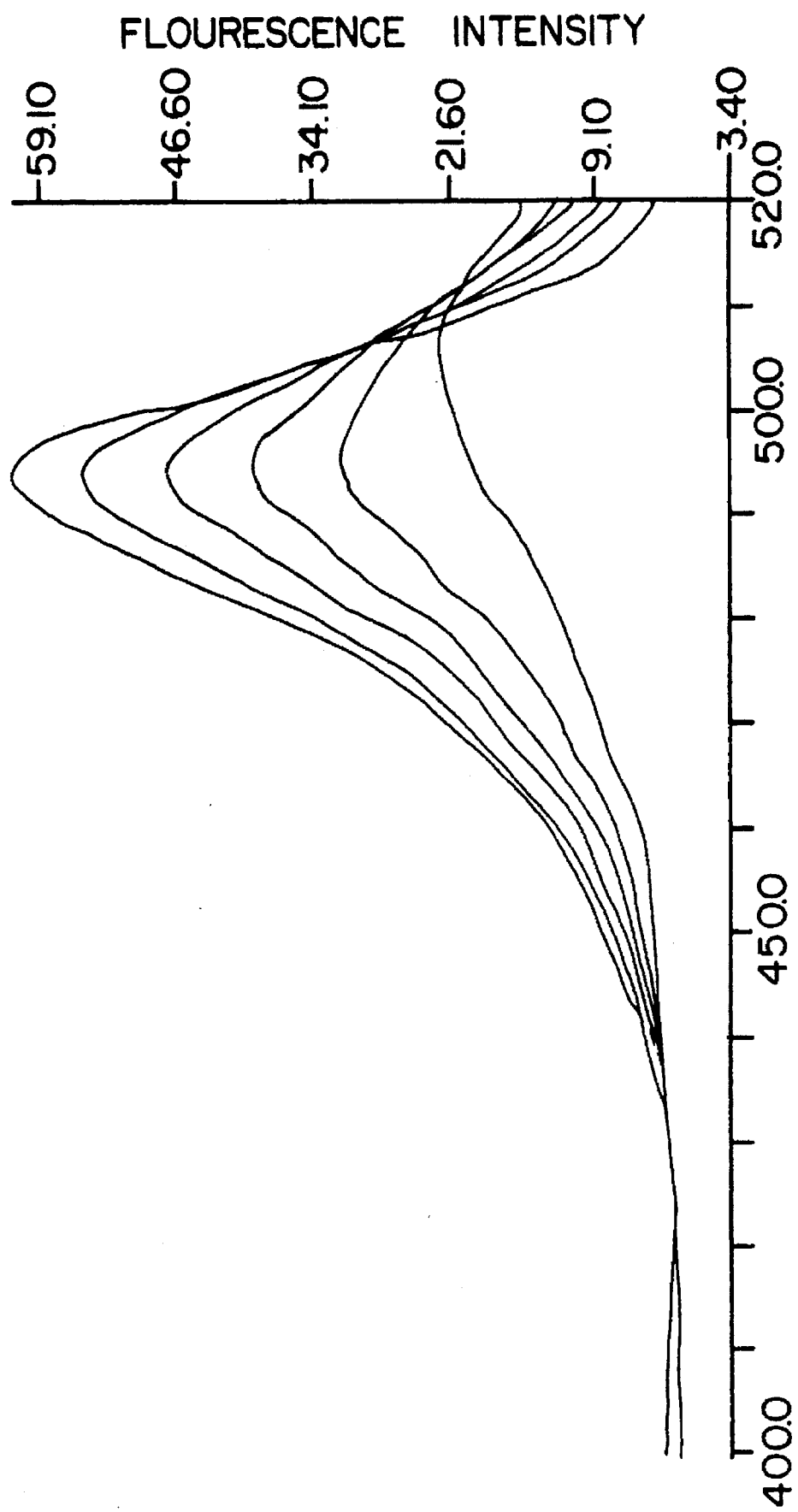

FIG. 5 illustrates the excitation spectrum resulting in the a mixture of QM212 with fluorescein using amounts ranging from 0 to 7.0 nM QM212. The excitation spectrum arcs are expressed as fluorescence intensity emitted after excitation over a range of wavelengths from 400 to 520 nm. Emission was measured at 530 nm. A 5 nm band width was used for both excitation and emission measurements. The data show that as more QM212 is added to the fluorescein solution, the amount of excitation is reduced, quenching the fluorescence excitation by about 80% (maxima to maxima). As QM212 binds fluorescein, the excitation maxima shifts from about 493 nm to about 507 nm.

Figure 6:
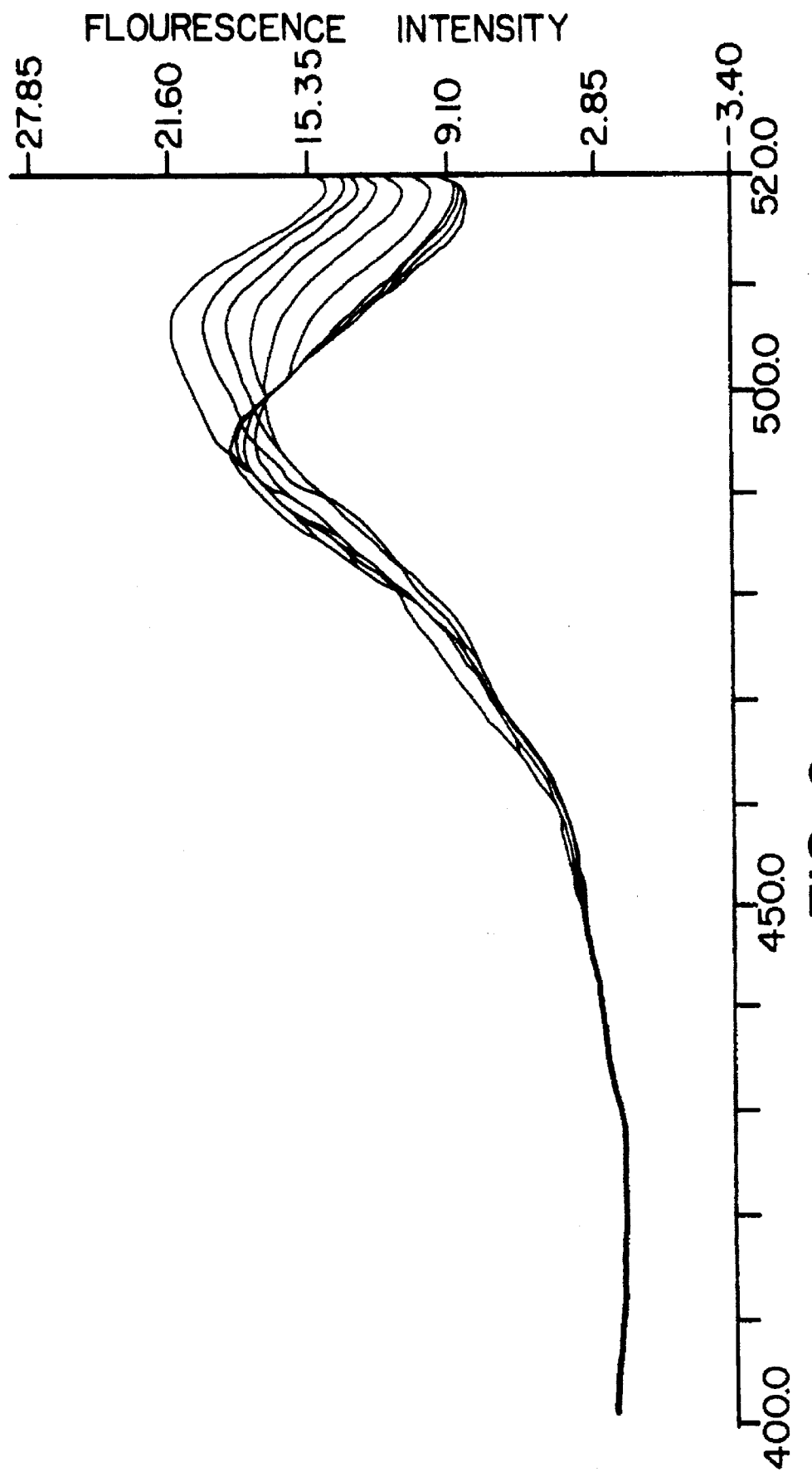

FIG. 6 illustrates the effects of Cu(II) on fluorescein excitation spectrum measured with fluorescein-bound QM212. Various amounts of Cu(II), ranging from 0 to 30 µM, were added to solution containing 15 nM sodium phosphate, pH 6.0, 7.0 nM of fluorescein and 7.7 µM of QM212. The excitation spectra were measured as described above in FIG. 5.

Figure 7A:
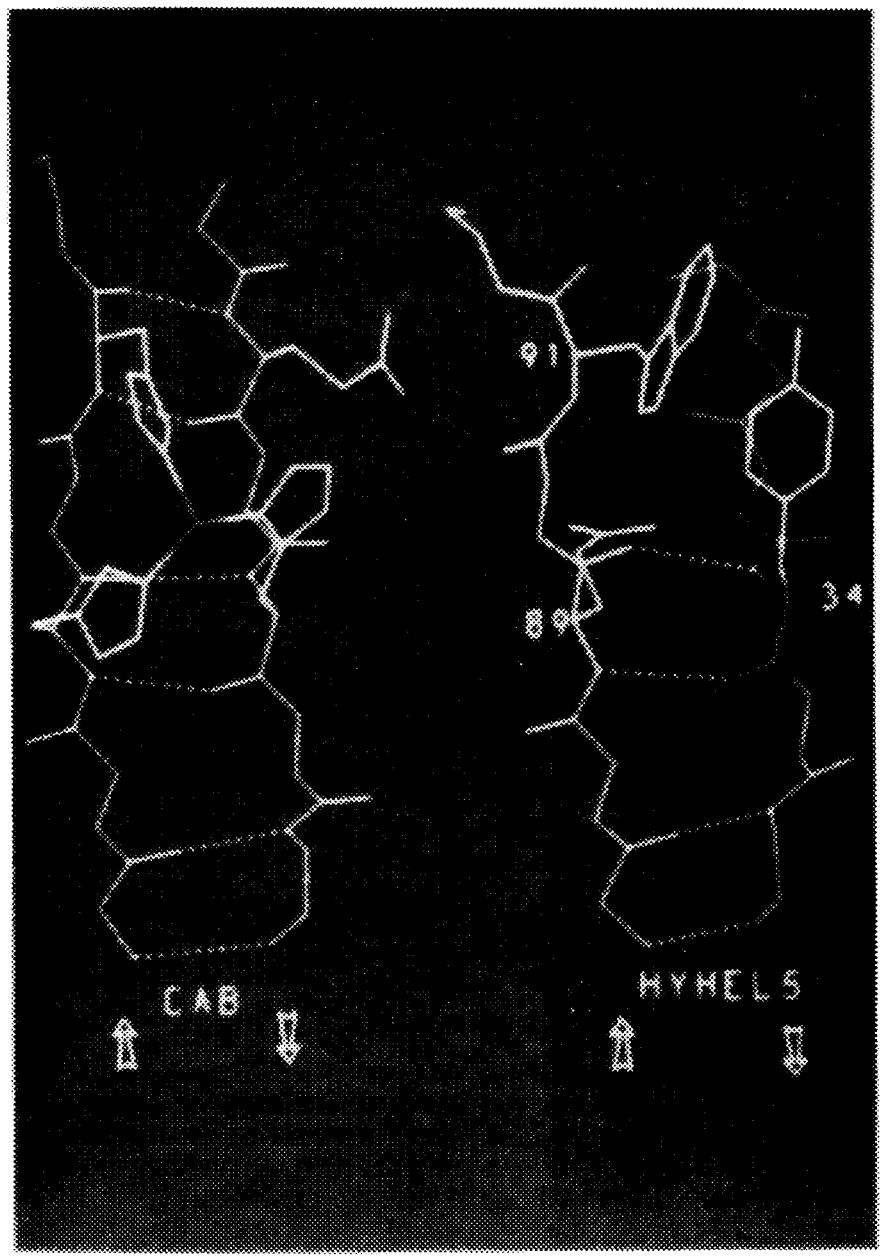

FIG. 7A illustrates the zinc-binding site of carbonic anhydrase (CAB) and the metal binding site introduced into the L1-L3 site of the antibody HyHEL5. A comparison of the zinc ligands of CAB by [Kannan et al., Proc. Natl. Acad. Sci. USA, 72:51–55 (1975)], in the left panel with the residues of the L1-L3 site in the HyHEL5 structure by [Sheriff et al., Proc. Natl. Acad. Sci. USA, 84:8075–8079 (1987)] in the right panel shows the similarity of hydrogen-bonding antiparallel β-strands, $C_\alpha$-$C_\beta$ bond directions, and placement of side chains. All other known antibody structures shared the arrangement seen in HyHEL5 in this region. Arrows indicate the direction of the polypeptide chain.

Figure 7B:
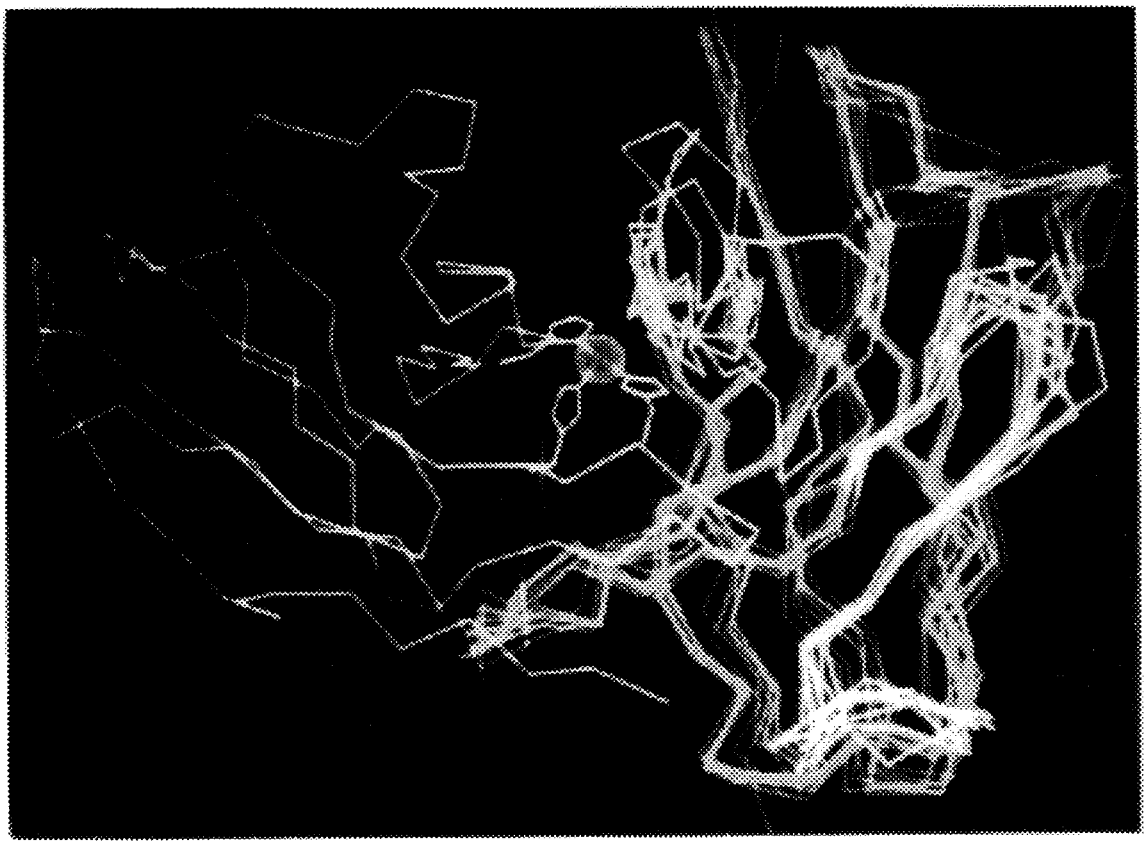

FIG. 7B illustrates the general L1-L3 zinc site in combination with a library of heavy chains to form a variety of zinc cofactor sites in the antibody $F_V$. The model of the HyHel5 $F_V$ $C_\alpha$ backbone with the CAB zinc-binding site built into $V_L$ is combined with superimposed $C_\alpha$ backbones of $V_H$ domains of antibodies HyHEL5, HyHEL10, Newm, J539, HEd10, Kol, D1.3 and McPC603. The $C_\alpha$ and $C_\beta$ atoms of CAB zinc-ligating residues 94, 96, and 119 were superimposed onto the corresponding atoms of HyHEL5 $V_L$ residues 89, 91 and 34, respectively, with a RMS deviation between the two structures of 0.57 Å for the six atoms. The three histidine ligands placed the zinc ion (shown by a sphere) at the bottom of the binding pocket between L3 and H3.

DETAILED DESCRIPTION OF THE INVENTION

A. Definitions

Amino Acid Residue: The amino acid residues described herein are preferred to be in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature as described in J. Biol. Chem., 243:3552–59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino acid residues or to a amino-terminal $NH_2$ group or to a carboxy-terminal COOH group.

Polypeptide: refers to a linear series of amino acid residues connected to one another by peptide bonds between the alpha-amino group and carboxy group of contiguous amino acid residues.

Protein: refers to a linear series of greater than 50 amino acid residues connected one to the other as in a polypeptide.

Synthetic polypeptide: refers to a chemically produced chain of amino acid residues linked together by peptide bonds that is free of naturally occurring proteins and fragments thereof.

Antibody Molecule: The phase "antibody molecule" in its various grammatical forms as used herein contemplates both an intact immunoglobulin molecule and an immunologically active portion of an immunoglobulin molecule, i.e. molecules that contain an antibody combining site or paratope.

Antibody Combining Site: An "antibody combining site" is that structural portion of an antibody molecule that specifically binds (immunoreacts with) antigen and is comprised of variable and hypervariable regions of both the heavy and light chains. The term "immunoreact" in its various forms means specific binding between an antigenic determinant-containing molecule and a molecule containing an antibody combining site such as a whole antibody molecule or a portion thereof.

Antibody: The term antibody in its various grammatical forms refers to a composition containing antibody molecules.

Exemplary antibody molecules are intact immunoglobulin molecules, substantially intact immunoglobulin molecules, portions of an immunoglobulin molecule that contains the paratope, including those portions known in the art as Fab, Fab', F(ab')$_2$ and F(v), and single chain antigen binding proteins.

Fab and F(ab')₂ portions of antibody molecules are prepared by the proteolytic reaction of papain and pepsin, respectively, on substantially intact antibody molecules by methods that are well known. See for example, U.S. Pat. No. 4,342,566 to Theofilopolous and Dixon. Fab' antibody molecule portions are also well known and are produced from F(ab')₂ portions followed by reduction of the disulfide bonds linking the two heavy chain portions as with mercaptoethanol, and followed by alkylation of the resulting protein mercaptan with a reagent such as iodoacetamide.

Single Chain Antigen Binding Protein: A polypeptide, also referred to as a single chain antibody combining site molecule, composed of an immunoglobulin light chain variable region amino acid sequence (VL) tethered to an immunoglobulin heavy chain variable region amino acid sequence (VH) by a peptide that links the carboxy terminus of the VL sequence to the to the amino terminus of the VH sequence. See for example, Bird et al., *Science*, 242:423–426 (1988). (The teachings of the references cited herein are hereby incorporated by reference.)

Immunoreaction Conditions: Immunoreaction conditions are those that maintain the immunological activity of a metalloantibody of this invention. Those conditions include a temperature range of about 4 degrees C. (4C.) to about 45C., preferably about 37C., a pH value range of about 5 to about 9, preferably about 7 and an ionic strength varying from that of distilled water to that of about one molar sodium chloride, preferably about that of physiological saline. Methods for optimizing such conditions are well known in the art.

Metal: The term "metal" in the context of a metal binding site refers to the metal cations disclosed herein that form a coordination complex with a metal binding protein.

Monoclonal Antibody: The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen, e.g., a bispecific monoclonal antibody.

Nucleotide: A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence", and is represented herein by a formula whose left to right orientation is in the conventional direction of 5'-terminus to 3'-terminus.

Polynucleotide: A nucleic acid molecule comprising a polymeric unit of DNA or RNA having a sequence of two or more operatively linked nucleotides that form a single linear strand of nucleotides, also referred to as an oligonucleotide.

Duplex: A double-stranded nucleic acid molecule consisting of two strands of complementary polynucleotide hybridized together by the formation of a hydrogen bond between each of the complementary nucleotides present in a base pair of the duplex. Because the nucleotides that form a base pair can be either a ribonucleotide base or a deoxyribonucleotide base, the term "duplex" referring to either a DNA—DNA duplex comprising two DNA strands, or a RNA-DNA duplex comprising one DNA and one RNA strand.

Base Pair (bp): A partnership of adenine (A) with thymine (T), or of cytosine (C) with guanine (G) in a double stranded DNA duplex.

Nucleic Acid: A term to refer to any of a class of molecules that includes ribonucleic acid (RNA), deoxyribonucleic acid (DNA) in its single or double stranded forms, and polynucleotides.

DNA segment: A DNA—DNA duplex having a preselected conserved nucleotide sequence and a sequence coding for a metal binding protein of the present invention.

B. Metal Binding Protein

The present invention contemplates a protein that has the ability to complex with (bind) a metal cation through ligands (contacts) provided by contact amino acid residues in the protein that are presented in a geometry that coordinates the complexation of a metal cation.

The protein binds metal cation and is therefore referred to as a metal binding protein. A metal cation is bound by the contemplated protein because the protein is capable of forming a coordination complex with the metal cation in a manner analogous to the coordination complex formations found in other well known metalloproteins, such as carbonic anhydrase, superoxide dismutase and the like.

A metal binding protein of the present invention is comprised of a sequence of amino acid residues that defines a variable domain of an immunoglobulin.

An immunoglobulin represents a large family of molecules that include several types of molecules, such as IgD, IgG, IgA, IgM and IgE. An immunoglobulin is typically comprised of two heavy (H) and two light (L) chains with both a variable (V) and constant (C) domain present on each chain. Several different regions of an immunoglobulin contain conserved sequences on the basis of comparative studies of known sequences of heavy or light chains. Extensive amino acid and nucleic acid sequence data displaying exemplary conserved sequences have been compiled for immunoglobulin molecules by Kabat et al., in *Sequences of Proteins of Immunological Interest*, 4th Ed., National institutes of Health, Bethesda, Md. (1987).

Present understanding of the sites of an antibody molecule responsible for antigen-antibody binding indicates that part of the antibody combining site is formed by heavy chain hypervariable regions, and part of the combining site is formed by the light chain hypervariable regions. See for example, Getzoff et al., *Adv. Immunol.*, 43:1–98 (1988). Six loops of polypeptide comprise the hypervariable regions; three loops from the variable domain of the light chain (VL) and three loops from the variable domain of the heavy chain (VH) denoted L1, L2, L3 and H1, H2, H3 respectively. See for example, Chothia et al., *Nature*, 342:877–883 (1989). The hypervariable regions are also known as complementarity determining regions, or CDR's.

Comparative studies of the known three dimensional structure of numerous antibody molecules have identified that each hypervariable region adopts one of a few main chain conformations or canonical structures. Using sequence homologies, the amino acid residue sequence of a heavy or light chain can be aligned with the sequence of a known immunoglobulin heavy or light chain structure, respectively, the hypervariable region loops and specific amino acid residue positions within the loops, of the heavy or light chain can be reproducibly identified.

Thus, for example, a L1, L2 or L3 loop structure (CDR L1, CDR L2 or CDR L3) can be reproducibly identified solely on the basis of sequence homologies to other immunoglobulin light chains, thereby locating the position of critical residue positions within the loop structure. Due to the existence of variation in the chain length for a particular immunoglobulin light chain, amino acid residue position numbers are referred to herein by a numbering scheme that is based on alignments using homologous sequences as described by Kabat et al., in *Sequences of Proteins of Immunological Interest*, 4th Ed., U.S. Department of Health and Human Services, National Institute of Health, Bethesda, Md. (1987). Specific residue number reference to the amino acid residue positions for particular residues, therefore, will be cited herein as "Kabat position number" or "Kabat amino acid residue position number" to connote a reproducibly identifiable residue position on a recognized CDR loop structure. Wherever position numbers are given, they refer to Kabat positions.

The variable domain of any immunoglobulin heavy or light chain molecule having the identifiable loop structures are useful in the present invention to produce a metal binding site. Representative of a variable domain of light chain in which a metal binding site was introduced by the present invention is the variable domain defined by the amino acid residue sequence shown in FIGS. 1A and 1B from residue 22 to residue 132.

A preferred metal binding protein having the above variable domain is the single chain antibody combining site molecule shown in FIGS. 1A and 1B from residue 1 to residue 263. The structure of single chain antigen binding proteins, i.e., single chain molecules having an antibody combining site or single chain antibody combining site molecules, have been described by Bird et al., *Science*, 224:423–426 (1988), and their preparation has also been described in U.S. Pat. No. 4,704,692 by Ladner.

A metal binding protein further includes a metal binding site on the protein when the protein is in a folded conformation, such that the protein forms by its folded structure a metal binding site and is capable of complexing with (binding to) a preselected metal cation. A metal binding site is formed by the geometric positioning of three metal ligands (contact sites) provided by the side chain residues of three contact amino acid residues to form coordinating ligands for complexing a metal cation. Thus the positioning of three contact amino acid residues in the amino acid sequence of an immunoglobulin variable domain defines a metal binding site.

The structure and stereochemistry of protein-metal interactions in metalloproteins is generally well understood. See for example, Freeman et al., *Adv. Protein Chem.*, 22:257–424 (1967); Kannan et al., *Annals. NY Acad. Sci.*, 429:49 (1984); and Tainer et al., *J. Mol. Biol.*, 160:181–217 (1982).

The metal ligands (contact sites) for binding a metal cation to a metal binding site on a protein of this invention are positioned at three locations to provide three ligand contact points typically required for a metal cation coordination complex. Representative coordination complex geometries for the metal ligands can be tetrahedral, square planar or trigonal. However, tetrahedral geometries are preferred. Representative coordination metal complexes of the preferred tetrahedral coordinating geometry are shown by the structure of the zinc(II) complex in the enzyme superoxide dismutase or the zinc(II) complex in carbonic anhydrase. See Tainer et al., *J. Mol. Biol.*, 160:181–217 (1982); and Kannan et al., *Annals. NY Acad. Sci.*, 429:49 (1984). In these examples, although a metal cation presents four potential contact sites, typically three participate in the metal-ligand contact, and the fourth site on the metal cation is free to participate in electron exchanges or sharing with solvent or solute in solution having access to the complexed metal. Similarly, in the present metal binding protein, three contact amino acid residues (ligand contact sites) participate in complexing the metal cation.

An amino acid residue that occupies one of the three amino acid residue positions to provide a metal ligand contact site in a metal binding site is referred to as a contact amino acid residue. Amino acid residues suitable for use as contact amino acid residues are known in the art of metalloprotein biochemistry and include histidine, aspartic acid, cysteine, glutamic acid and the like residues known to provide a ligand for metal cations in metalloproteins. In one preferred embodiment, the three contact amino acid residues are two histidines and a third residue selected from the group of histidine, aspartic acid, cysteine and glutamic acid. Particularly preferred is the use of histidine residues for all three contact amino acid residues.

By the present invention it was determined that immunoglobulin heavy and light chain molecules each contain sites for positioning three contact amino acid residues suitable to produce a metal ligand binding site. These sites can be reproducibly located as to present metal cation ligand contacts at the proper coordinates for forming a metal binding site because the location of the critical amino acid residue position for forming a metal binding hypervariable regions of either a heavy or light chain can be reproducibly identified in the CDR loop structure due to their conserved features. See Getzoff et al., *Adv. Immunol.*, 43:1–98(1988); and Chothia et al. *Nature* 342:877–883 (1989). Therefore, any immunoglobulin heavy or light chain molecule can be modified to contain a metal binding site according to the teachings of this invention once the contact amino acid residue positions are identified by the Kabat position number as described herein.

Contact amino acid residue positions defining a metal binding site have been discovered by the present invention. Contact amino acid residues can therefore be engineered into a variable domain of an immunoglobulin heavy or light chain molecule to form a metal binding site and their positions are summarized in Table 1.

Thus, in one embodiment the amino acid residue positions used to provide three metal ligand contact sites are located in specific positions of the amino acid sequence that defines the variable domain of the immunoglobulin light chain molecule.

In one light chain embodiment, the variable domain includes a L1 region and a L3 region and the three contact amino acid residues are located at any three of the four amino acid residue positions 32, 34, 89 and 91.

Thus, one preferred metal binding site includes three contact amino acid residues occupying amino acid residue positions 32, 34 and 89; positions 32, 34 and 91; positions 32, 89 and 91; or 34, 89 and 91 of an immunoglobulin light chain variable domain. A preferred and exemplary metal binding site is formed by using histidine as the contact amino acid residue at positions 34, 89 and 91, and is described in more detail in Example 1a and FIGS. 1A and 1B. In the exemplary metal binding protein, whose complete amino acid residue sequence is shown in FIGS. 1A and 1B, the contact amino acid residues having Kabat position number of 34, 89 and 91 are located at the amino acid residue positions 60, 115 and 117, respectively, of the single chain antigen binding protein (QM212) shown in FIG. 1.

Several features of the CDR L1 and CDR L3-containing variable domain of the light chain provide an optimum environment for positioning a metal binding site on the claimed protein as disclosed herein. The L1 and L3 regions form anti-parallel strand main-chain structures hydrogen bond between strands at several points. This feature provides a beta sheet structure that is reproducible and readily identifiable in all light chain variable domains. It also provides stabilization to facilitate proper atomic distances so that the preselected sites for contact amino acid residues are properly located to form a tetrahedral array for presenting ligands to complex the metal cation.

Hydrogen bonds are typically found between main-chain atoms of residue pair 89 and 34, or pair 91 and 32, that stabilize the L3 and L1 main chain structures, respectively.

In the embodiment utilizing contact amino acid residues at positions 34, 89 and 91 of the light chain, a metal binding protein of the present invention preferably includes either glycine or a non-polar amino acid residue at the amino acid residue position 36 of the light chain variable region sequence, where the non-polar residue is an amino acid residue having fewer size chain atoms than tyrosine, and is not proline. Preferred residues are leucine, valine and alanine. In particularly preferred embodiments, a metal binding protein has a leucine residue at position 36 in the light chain variable domain.

In another light chain embodiment, the variable domain includes a L3 region and the three contact amino acid residues are located at amino acid residue positions 90, 92 and 97. Hydrogen bonds are preferably located between the main-chain atoms of residue pair 90 and 97 to stabilize the L3 main-chain structure.

Another light chain embodiment includes a L3 region in the variable domain containing the three contact amino acid residues at amino acid residue positions 89, 91 and 96.

A related light chain embodiment includes an L2 region in the variable domain containing the three contact amino acid residues at amino acid residue positions 50, 53 and 55.

Another light chain embodiment includes a L1 region and a L3 region of a light chain variable domain and contains three contact amino acid residues at amino acid residue positions 27d, 29 and 93. Positions 27d and 29 are located in the L1 region. The Kabat position 27d connotes an amino acid residue position that is four amino acid residues away from position 29 in the direction towards the amino terminus of the light chain.

In another embodiment the amino acid residue positions used to provide three metal ligand contact sites are located in specific positions of the amino acid sequence that defines the variable domain of the immunoglobulin heavy chain molecule.

In one heavy chain embodiment, the variable domain includes a H1 region and a H3 region and the three contact amino acid residues are located at amino acid residue positions 33, 35 and 95. Hydrogen bonds are preferably located between the main-chain atoms of the residue pair 33 and 95 to stabilize the H1 and H3 main-chain structures.

In another heavy chain embodiment, the variable domain includes a H1 region and a H2 region and the three contact amino acid residues are located at any three of the four amino acid residue positions 33, 35, 50 and 52.

Another heavy chain embodiment includes a H1 region and a H2 region in the variable domain containing the three contact amino acid residues at amino acid residue positions 31, 33 and 52.

A related heavy chain embodiment includes a H2 region in the variable domain containing three contact amino acid residues at any three of the four amino acid residue positions 50, 52, 56 and 58. Hydrogen bond pairs are preferably located between the main-chain atoms of residue pair 50 and 58 to stabilize the H2 main-chain structure.

In another heavy chain embodiment, the variable domain includes a H2 region, and the three contact amino acid residues are located at the amino acid residue positions 50, 58 and 60. Hydrogen bond pairs are preferably located between the main-chain atoms of residue pair 50 and 58 to stabilize the H2 main-chain structure.

Another heavy chain embodiment includes a H3 region in the variable domain containing the three contact amino acid residues at amino acid residue positions 95, 101x and 101x-2. The position designation "101x" connotes alternative positions of either Kabat position number 101 or the amino acid residue position preceding position 101, i.e., the position one residue away from position 101 and in the direction towards the amino terminus of the heavy chain. The position designation "101x-2" connotes alternative positions that depend on the position indicated by the term "101x". If 101x is position 101, then 101x-2 is a position two residues away from position 101 in the direction towards the amino terminus of the heavy chain. If 101x is the position preceding 101 by one residue, then 101x-2 is a position three residues away from position 101 in the direction towards the amino terminus of the heavy chain.

C. Methods of Binding Metal Cations

The present invention contemplates a method of separating a metal cation from a fluid sample containing the metal cation. This metal separating method includes the following steps:

1. Admixing a fluid sample containing metal cations with a metal binding protein to form a binding admixture.
2. Maintaining the binding admixture for a time period sufficient for the metal cation to bind the metal binding protein and form a metal cation protein complex.
3. Removing the metal cation protein complex from the binding admixture and thereby separating the metal cation from the fluid sample.

The amount of time required for the metal cation to bind the metal binding protein will depend upon at least the particular metal binding protein employed, the binding constant exhibited by the metal binding protein and the concentration of the metal. The metal cation-protein complex is formed when at least one metal cation associates with the metal binding protein and becomes bound to that protein to form a metal cation protein complex. The metal cation-protein complex is then removed from the binding admixture thereby separating the metal cation from the fluid sample. The complex may be removed using methods well known to those skilled in the art and include mechanically removing, filtration, sedimentation and other separation means.

In other preferred embodiments, the metal binding protein is affixed to a solid support such as plastic, nitrocellulose, nylon-based membranes, or microtitre plate wells. When the metal binding protein is affixed to a solid support, the metal cation-protein complex formed is immobilized on the solid support and is part of a solid phase.

The metal binding protein is typically affixed to the solid matrix by adsorption from an aqueous medium although other modes of affixation, well known to those skilled in the art, can be used.

Useful solid matrices (solid supports) are also well known in the art. Such materials are water insoluble and include the cross-linked dextran available under the trademark SEPHA-DEX from Pharmacia Fine Chemicals (Piscataway, N.J.); agarose; beads of polystyrene, beads about 1 micron to about 5 millimeters in diameter are available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

In preferred embodiments, the metal binding protein of the present invention contains an antibody combining site that is capable of immunoreaction with a preselected antigen. Thus a convenient method for removing a metal cation-protein complex that can immunoreact with a preselected antigen from a binding admixture is to (1) admix the binding admixture with a solution containing the preselected antigen to form an immunoreaction admixture, (2) maintain the immunoreaction admixture for a time period sufficient for an immunoreaction product to form and (3) removal of the immunoreaction product from the immunoreaction admixture, thereby removing the metal cation protein complex from the binding admixture. In preferred embodiments, the preselected antigen is immobilized to a solid support to facilitate removal of the immunoreaction product from the immunoreaction admixture (liquid phase). Solid supports useful for immobilizing the preselected antigen are the same solid supports described for use in immobilizing the metal binding protein.

D. Methods of Preparing a Metal Binding Protein

A metal binding protein of the present invention can be prepared by the general methods of molecular cloning of recombinant DNA molecules, manipulation of those cloned molecules and protein expression using the manipulated DNA molecules. An overview of the method involves the following elements:

1. Obtaining a gene coding for a sequence of amino acid residues that define a variable domain of an immunoglobulin molecule.
2. Determining the sequence of the gene to locate the regions that code for amino acid residue positions disclosed herein that are suitable for introducing a nucleotide mutation to encode a desired contact amino acid residue and produce a metal binding site.
3. Modifying the nucleotide base sequence of the gene to encode metal ligand contact residues at three of the four metal ligand contact site residue positions within the variable domain.
4. Inserting the modified nucleotide base sequence into an expression vector.
5. Expressing the metal binding protein from the modified gene using the expression vector in a suitable host.
6. Isolating the expressed protein from the expression medium.

A gene may be obtained by a variety of means. A DNA segment containing a preselected nucleotide sequence may be prepared by chemical synthesis using, for example, the phosphotriester method of Matteucci et al., *J. Am. Chem. Soc.*, 103:3185 (1981). Once prepared, the DNA segment is included into a recombinant DNA vector that is useful to manipulate and express the gene encoding a metal binding protein.

A DNA segment containing a preselected nucleotide sequence may also be assembled from a number of chemically synthesized polynucleotides designed to form a particular DNA segment when hybridized together to form a double stranded DNA segment. The double stranded DNA segment is then ligated together using T4DNA ligase and inserted into an appropriate expression vector.

Alternatively, a gene coding for immunoglobulin molecules, particularly variable domains of light chain, can be obtained by molecular cloning of messenger RNA (mRNA) or genomic DNA.

Methods for isolating a gene are well known in the art. See, for example, "Guide To Molecular Cloning Techniques", in *Methods In Enzymology*, Volume 152, Berger and Kimmel, eds. (1987); and *Current Protocols in Molecular Biology*, Ausubel et al., eds., John Wiley and Sons, NY (1987), whose disclosures are herein incorporated by reference.

Genes useful in practicing this invention include genes coding for a sequence of amino acid residues defining a variable domain contained in immunoglobulin products, immunoglobulin molecules, Fab fragments, $F_V$ fragments and abzymes. Particularly preferred are genes coding for intact immunoglobulin light chain variable domains. In one embodiment, the genes coding for the immunoglobulin light chain variable region of an immunoglobulin capable of binding a preselected antigen are used. These genes are isolated from cells obtained from a vertebrate, preferably a mammal, which has been immunized with an antigenic ligand (antigen) against which activity is sought, i.e., a preselected antigen. The immunization can be carried out conventionally and antibody titer in the animal can be monitored to determine the state of immunization desired, which corresponds to the affinity or avidity desired. Partially immunized animals typically receive only one immunization and cells are collected therefrom shortly after a response is detected. Fully immunized animals display a peak titer which is achieved with one or more repeated injections of the antigen into the host mammal, normally at two to three week intervals.

Usually three to five days after the last challenge, the spleen is removed and the genes coding for immunoglobulin heavy and immunoglobulin light chain are isolated from the rearranged B cells present in the spleen using standard procedures. See *Current Protocols in Molecular Biology*, Ausubel et al., eds., John Wiley and Sons, NY (1987); and *Antibodies: A Laboratory Manual*, Harlowe and Lane, eds., Cold Spring Harbor, N.Y. (1988).

Genes coding for $V_H$ and $V_L$ polypeptides can be derived from cells producing IgA, IgD, IgE, IgG or IgM, most preferably from IgM and IgG, producing cells. Methods for preparing fragments of genomic DNA from which immunoglobulin variable region genes can be cloned are well known in the art. See for example, Herrmann et al., *Methods in Enzymol.*, 152:180–183 (1987); Frischauf, *Methods in Enzymol.*, 152:183–190 (1987); Frischauf, *Methods in Enzymol.*, 152:199–212 (1987); and DiLella et al., *Methods in Enzymol.*, 152:199–212 (1987).

Genes coding for a variable domain of an immunoglobulin light chain can be isolated from either the genomic DNA containing the gene as described above or from the mRNA which codes for the variable domain. The difficulty in using genomic DNA is in juxtaposing the sequences coding for a polypeptide where the sequences are separated by introns. The DNA fragment(s) containing the proper exons must be isolated, the introns excised, and the exons spliced together in the proper order and orientation. For the most part, this will be difficult so the alternative technique employing mRNA will be the method of choice because the sequence is contiguous (free of introns) for the entire polypeptide. Methods for isolating mRNA coding for peptides or proteins are well known in the art. See, for example, *Current Protocols in Molecular Biology*, Ausubel et al., John Wiley and Sons, NY (1987); *Guide to Molecular Cloning Techniques*, in *Methods In Enzymology*, Volume 152, Berger and Kimmel, eds. (1987), and *Molecular Cloning: A Laboratory Manual, Second Edition*, Maniatis et al., eds., Cold Spring Harbor, N.Y. (1989).

Genes coding for both heavy and light chain variable regions can be obtained from mRNA and/or genomic DNA using the polymerase chain reaction and various primers. See, for example, Orlandi et al., *Proc. Natl. Acad. Sci. USA*, 86:3833–3837 (1989); Sastry et al., *Proc. Natl. Acad. Sci., USA*, 86:5728–5732 (1989); Ward et al., *Nature*, 341:544 (1989); Huse et al., *Science*, 246:1275–1281 (1989) and *PCR Protocol: A Guide to Methods and Applications*, Innis et al., eds., Academic Press, London (1990).

Modifications to the metal binding protein coding nucleotide sequence may be introduced using any of the well known methods of site-directed mutagenesis. See, for example, Smith, *Ann. Rev. Genet.*, 19:423–463 (1985); Kunkel et al., *Proc. Natl. Acad. Sci., USA*, 82:488–492 (1985); and Kunkel et al., *Meth. Enzymol.*, 154:367–382 (1987).

The modified nucleotide sequence capable of encoding a metal binding protein is typically linked to an expression vector. Expression vectors compatible with the host cells, preferably those compatible with either eucaryotic or procaryotic host cells are used to express the genes of the present invention. Expression vectors compatible with mammalian, insect, plant or bacterial cells are particularly useful.

In preferred embodiments, an expression vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the metal binding protein nucleotide sequence in a bacterial host cell, such as *E. coli*, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.) and pPL and pKK223 available from Pharmacia, Piscataway, N.J.

Expression vectors compatible with eucaryotic cells, preferably those compatible with vertebrate cells, can also be used to express the nucleotide sequence coding for a metal binding protein of the present invention. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1pML2d (International Biotechnologies, Inc.), and pTDT1 (ATCC, #31255).

In preferred embodiments, the eucaryotic cell expression vectors used to express the nucleotide sequence coding for a metal binding protein of the present invention include a selection marker that is effective in an eucaryotic cell, preferably a drug resistance selection marker. A preferred drug resistance marker is the gene whose expression results in neomycin resistance, i.e., the neomycin phosphotransferase (neo) gene. Southern et al., *J. Mol. Appl. Genet.*, 1:327–341 (1982).

The use of retroviral expression vectors to express a nucleotide sequence coding for a metal binding protein from the present invention is also contemplated. As used herein, the term "retroviral expression vector" refers to a DNA molecule that includes a promoter sequence derived from the long terminal repeat (LTR) region of a retrovirus genome.

In preferred embodiments, the expression vector is typically a retroviral expression vector that is preferably replication-incompetent in eucaryotic cells. The construction and use of retroviral vectors has been described by Sorge, et al., *Mol. Cell. Biol.*, 4:1730–37 (1984).

A variety of methods have been developed to operatively link nucleotide sequences to vectors via complementary cohesive termini. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Synthetic linkers containing one or more restriction sites provide an alternative method of joining the nucleotide segment to vectors. The nucleotide segment, generated by endonuclease restriction digestion as described earlier, is treated with bacteriophage T4 DNA polymerase of *E. coli* DNA polymerase I, enzymes that remove protruding, 3', single-stranded termini with their 3'–5' exonucleolytic activities and fill in recessed 3' ends with their polymerizing activities. The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies, Inc., New Haven, CAN.

Typical expression vectors useful for expression of genes in plants are well known in the art and include vectors derived from the tumor-inducing (Ti) plasmid of *Agrobacterium tumefaciens* described by Rogers et al., *Meth. in Enzymol.*, 153:253–277 (1987). However, several other expression vector systems are known to function in plants. See for example, Verma et al., PCT Publication. No. WO87/00551; and Cocking and Davey, *Science*, 236:1259–1262 (1987).

The expression vectors described above contain expression control elements including the promoter. The metal binding protein coding nucleotide sequence is operatively linked to the expression vector to allow the promoter sequence to direct RNA polymerase binding and synthesis of the desired polypeptide coding gene. Useful in expressing the metal binding protein coding nucleotide sequences are promoters which are inducible, viral, synthetic, constitutive, temporally regulated, spatially regulated, and spatiotemporally regulated.

The choice of which expression vector and ultimately to which promoter a metal binding protein coding nucleotide sequence (gene) is operatively linked depends directly, as is well known in the art, on the functional properties desired, e.g. the location and timing of protein expression, and the host cell to be transformed, these being limitations inherent in the art of constructing recombinant DNA molecules. However, an expression vector useful in practicing the present invention is at least capable of directing the replication, and preferably also the expression of the polypeptide coding gene included in the DNA segment to which it is operatively linked.

In preferred embodiments, the expression vector used to express the metal binding protein coding gene includes a selection marker that is effective in a plant cell, preferably a drug resistance selection marker. A preferred drug resistance marker is the gene whose expression results in kanamycin resistance, i.e., the chimeric gene containing the nopaline synthase promoter, Tn5 neomycin phosphotransferase II and nopaline synthase 3' nontranslated region described by Rogers et al., in *Methods For Plant Molecular Biology*, a Weissbach and H. Weissbach, eds., Academic Press Inc., San Diego, Calif. (1988). A useful plant expression vector is commercially available from Pharmacia, Piscataway, N.J.

A variety of methods have been developed to operatively link DNA to vectors via complementary cohesive termini. For instance, complementary homopolymer tracks can be added to the DNA segment to be inserted and to the vector DNA. The vector and DNA segment are then joined by hydrogen bonding between the complementary homopolymeric tails to form recombinant DNA molecules.

Alternatively, synthetic linkers containing one or more restriction endonuclease sites can be used to join the nucleotide sequence to the expression vector. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteriophage T4 DNA ligase. Thus, the products of the reaction are DNA segments carrying synthetic linker sequences at their ends. These DNA segments are then cleaved with the appropriate restriction endonuclease and ligated into an expression vector that has been cleaved with an enzyme that produces termini compatible with those of the synthetic linker. Synthetic linkers containing a variety of restriction endonuclease sites are commercially available from a number of sources including New England BioLabs, Beverly, Mass.

Methods for introducing metal binding protein coding genes into plants include Agrobacterium-mediated plant transformation, protoplast transformation, gene transfer into pollen, injection into reproductive organs and injection into immature embryos. Each of these methods has distinct advantages and disadvantages. Thus, one particular method of introducing genes into a particular plant species may not necessarily be the most effective for another plant species.

The present invention also relates to a host cell transformed with a recombinant DNA molecule of the present invention preferably a nucleotide sequence capable of expressing a soluble form of a metal binding protein. The host cell can be either procaryotic or eucaryotic. Bacterial cells are preferred procaryotic host cells and typically are a strain of *E. coli* such as, for example, the *E. coli* strain DH5 available from Bethesda Research Laboratories, Inc., Bethesda, Md. Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61 and NIH Swiss mouse embryo cells NIH/3T3 available from the ATCC as CRL 1658. Transformation of appropriate cell hosts with a recombinant DNA molecule of the present invention is accomplished by well known methods that typically depend on the type of vector used. With regard to transformation of procaryotic host cells, see, for example, Cohen et al., *Proc. Natl. Acad. Sci. USA*, 69:2110 (1972); and Maniatis et al., *Molecular Cloning, A Laboratory Mammal*, Cold Spring Harbor Laboratory, Cold Spring Harbor, N.Y. (1982). With regard to transformation of vertebrate cells with retroviral vectors containing rDNAs, see, for example, Sorge et al., *Mol. Cell. Biol.*, 4:1730–37 (1984); Graham et al., *Virol.*, 52:456 (1973); and Wigler et al., *Proc. Natl. Acad. Sci. USA*, 76:1373–76 (1979).

Metal binding proteins produced in various host cells by an expression vector may be isolated by a variety of well known means including homogenization of the host cell followed by isolation of the metal binding protein or isolation of metal binding protein excreted into the medium in which the host cells are grown.

An isolated protein is a protein that is substantially free of other cellular proteins found with that protein in nature. For example, an isolated metal binding protein is substantially free of other *E. coli* host cell proteins that are present in the *E. coli* host cell that produced the metal binding protein. An isolated metal binding protein is also substantially free of proteins that do not have an identical amino acid residue sequence.

E. Metalloprotein

A metal binding protein of the present invention becomes a metalloprotein when it is complexed with a metal cation.

Metal cations (cofactor cations) suitable for complexing with a metal binding protein of this invention are any of the transition state metals of the periodic table, and the non-transition state metals calcium (Ca), zinc (Zn), cadmium (Cd), mercury (Hg), strontium (Sr), and barium (Ba), which metals have the capacity to occupy a tetrahedral oxidation state and thereby complex with said protein through coordinated ligands provided by the three contact amino acid residues on the metal binding protein. Preferred metal cations for use in a metalloprotein of this invention are divalent cations, preferably $Cu(II)$, $Zn(II)$, $Ni(II)$, $Co(II)$, $Fe(II)$, $Ag(II)$, $Mn(II)$ or $Cd(II)$, and more preferably $Cu(II)$.

Metalloproteins are formed by preparing a metal binding protein of the present invention, and then exposing the metal binding protein to a selected metal cation, preferably in a buffered aqueous medium, for a time sufficient to allow a metal-protein coordination complex to form. Preferred is the metalloprotein prepared and described in the Examples.

Metalloproteins may also be formed by admixing a metal binding protein of the present invention with another metalloprotein such as calmodulin that is complexed with calcium or metallothionein complexed with cadmium. The metalloproteins of the present invention would then complex with the cation donated from the other metalloprotein.

F. Metal Binding Antibody Molecules and Metalloantibodies

The present invention also contemplates a metal binding protein of this invention that has the capacity to immunoreact with a preselected antigen.

A metal binding protein contains an immunoglobulin light chain variable domain as disclosed herein. In one embodiment, that metal binding protein can be present in association with a heavy chain variable domain as to form an antibody combining site and thereby have the capacity to immunoreact with antigen.

For example, a $V_H$ and $V_L$ encoding pair of genes can be isolated as disclosed herein for $V_L$ alone. The $V_L$ gene is then modified to contain a metal binding site, and the $V_L$ and $V_H$ genes are then co-expressed to produce $V_H$ and $V_L$ gene products which assemble into di- or multimeric protein complexes which have the capacity to form an antibody combining site and immunoreact with a preselected antigen.

Cloned genes encoding heavy and light chain immunoglobulin molecules have been repeatedly isolated, and then introduced into an expression medium that produces assembled antibody molecules comprised of both $V_H$ and $V_L$ that are capable of immunoreaction with the same specificity as the antibody produced by the antibody producing cell from which the immunoglobulin protein-encoding genes were isolated. See, for example Roberts et al., *Protein Engineering*, 1:59–65 (1986); Morrison, *Science*, 229:1202–07 (1985); U.S. Pat. No. 4,474,893; and published patent application Nos. EP 0125023, EP 0239400 and WO 89/00999.

For the isolation of an immunoglobulin heavy or light chain-encoding gene in the preparation of a metal binding antibody, the genes can be obtained from any cell that produces an antibody molecule that immunoreacts with a preselected antigen. A preferred cell is a hybridoma cell or an immunoresponding spleen cell.

For examples of general recombinant DNA cloning methods, see *Molecular Cloning*, Maniatis et al., Cold Spring Harbor, N.Y., (1982); *DNA Cloning*, Glover, ed., IRL Press, McLean, Va. (1985). For the genomic cloning and expression of immunoglobulin genes in lymphoid cells, see Neuberger et al., *Nature*, 312:604–8 (1984); Ochi et al., *Proc. Natl. Acad. Sci. USA*, 80:6351–55 (1987); and Oi et al., *Proc. Natl. Acad. Sci. USA*, 80:825–29 (1983). For cloning of immunoglobulin genes from hybridoma cells, and their expression in Xenopus oocytes, see Roberts et al., *Protein Engineering*, 1:59–65 (1986), and see Wood et al., *Nature*, 314:446–9 (1985) for their expression in yeast.

A metal binding antibody can also be produced from an immunological repertoire as described by Sastry et al., *Proc. Natl. Acad. Sci.*, 86:5728–5732 (1989); Huse et al., *Science*, 246:1275–1281 (1989). In this embodiment, a cloned gene encoding a protein that includes an immunoglobulin light chain variable domain ($V_L$) can be modified to contain a metal binding site as disclosed herein. Thereafter, the modified $V_L$ gene is combined with any of the $V_H$ gene counterparts present in the immunological repertoire. By this method a large number of combinations of $V_L$ (modified) plus $V_H$ (repertoire) can be prepared in which the antigenic specificity will vary based on which $V_H$ protein encoded by the repertoire is assembled with the $V_L$ protein having the metal binding site. The combinations are then screened for the ability to immunoreact with a predetermined antigen in the presence of a cofactor cation.

Also contemplated are the combination of a heavy chain variable region ($V_H$) that has been modified to contain a metal binding site of the present invention. The modified $V_H$ is combined with any of the $V_L$ counterparts present in the immunological repertoire. This method produces a large number of combinations of modified $V_H$ (modified) and $V_H$ (repertoire). The combinations are then screened for the ability to immunoreact with a predetermined antigen in the presence of a cofactor cation.

A single chain antigen binding molecule is a further embodiment for a metal binding antibody of this invention. In this embodiment, $V_H$ and $V_L$ are operatively linked by a peptide linker as described further herein, and the $V_L$ aspect contains a metal binding site. Exemplary of a single chain metal binding antibody is the protein QM212 described and prepared in Example 1.

The metal binding antibody molecules described herein are useful to selectively partition and/or remove metal cations from aqueous solutions by the metal cation binding methods disclosed herein. Advantage can be taken of the immunoreactivity of the antibody combining site aspect of a metalloantibody complex formed, so that preselected antigens can be used in the solid phase, for example, to remove metalloantibody complexes from the liquid phase.

In another embodiment, a metal binding antibody can immunoreact with an antigen that serves as an indicator of metal complex formation. For example, an antigen can be sensitive to the presence of a metal cation in the microenvironment of the antibody combining site and indicate complexation of the metal binding site with a metal cation. Chromophobic antigens such as fluorescein, for example, produce shifts in fluorescence when a metal cation is bound in a metal binding site of this invention adjacent to the antibody combining site.

G. Catalytic Metalloantibody

In another embodiment, the invention contemplates a metalloantibody of the present invention which has the capacity of promoting a predetermined chemical reaction, i.e., a catalytic metalloantibody. In this embodiment, a preselected antigen with which the antibody combining site immunoreacts is also a substrate for a reaction that is promoted by the metalloantibody.

In preferred embodiments, the metal cation of a catalytic metalloantibody is Zn(II), and a preferred chemical reaction is the hydrolysis of a peptide bond.

Catalytic antibodies have been described by Tramontano et al., *Science*, 234:1566–1570 (1986); Pollack et al., *Science*, 234:1570–1573 (1986); Janda et al., *Science*, 241:1188–1191 (1988); and Janda et al., *Science*, 244:437–440 (1989).

EXAMPLES

The following examples are intended to illustrate, but not limit, the present invention.

1. Preparation of a Metal Binding Antibody Molecule

A. QM212 Expression Vector

The plasmid expression vector pQM212 contains a structural gene that encodes the amino acid residue sequence shown in FIGS. 1A and 1B for the protein QM212 and has the capacity to direct the expression of QM212 under conditions described below. The vector also contains the features shown in FIG. 2 including an ampicillin resistance gene (ampR), an M13 origin of replication (M13 Ori), and a lambda promoter (OL/PR) providing a binding site for the temperature sensitive lambda repressor for expressing the QM212 gene, in addition to containing the nucleotide base sequence shown in FIGS. 1A and 1B from base 1 to base 789 that encodes QM212.

QM212 is a single chain antigen binding protein having a metal binding site, and is derived from the 4-4-20/202 protein described by Bird et al., *Science*, 242:423–426 (1988). QM212 differs from 4-4-20/212 by amino acid substitutions at residue positions 60, 62, 115 and 117 to provide for contact amino acid residues, where three of these contact residues form a metal binding site. Four mutations were introduced into the gene encoding the 4-4-20/212 protein molecule by the in vitro mutagenesis techniques described by Sayels et al., *Nucl. Acids Res.*, 16:791–802 (1988). The substitution of Leu into residue position 36 in place of Tyr 36, although not required to introduce amino acid contact residues, was made to remove possible, but unverified, stearic interactions between His 89 and hydroxyl residue of Tyr 36. Thus, two mutations were introduced into CDR L3, converting a Ser to a His at both residue positions 115 and 117 using a single 30 base oligonucleotide. Two mutations were introduced into CDR L1 at residue position 60 converting an Arg to a His and at residue position 62 converting a Tyr to a Leu using a single 30 base oligonucleotide. The resulting plasmid containing the four substitutions was isolated and substitutions were verified by DNA sequencing.

B. Expression of QM212 Protein

Expression plasmid pQM212 was introduced into the *E. coli* cells, strain N99(C1857), by transformation, and successfully transformed cells were obtained and designated N99/pQM212. Plasmid pQM212 in *Escherichia coli* strain N99(C1857) designated QM212 #7 was deposited with the American Type Culture Collection (ATCC, Bethesda, Md.) on May 8, 1990, and was assigned an accession number 68321. About 1 milliliter (ml) of culture saturated with N99/pQM212 cells was inoculated into 400 mls of LB Amp medium (yeast extract 10 gm/L, peptone 10 gm/L, NaCl 5 gm/L, K2HPO4 10 gm/L, ampicillin 100 mg/L, pH 7.0) in a 2 liter (L) baffled flask and cultured at 30 Centigrade degrees (30C.) to form a bacterial culture. The optical density (O.D.) of the bacterial culture was periodically measured at 600 nanometer (nm) using LB Amp medium as a baseline of zero absorbance. When the O.D. of the bacterial culture reached about 3.0 O.D. units, after about 5 hours, the culture was transferred to a water bath at 50C. and maintained with agitation to rapidly raise the culture temperature to about 42–44C. The raising of the temperature allowed for induction of lambda repressor within the N99 (C1857) host cells, thereby activating the left operon promoter (OL/PR) present on pQM212 upon binding the lambda repressor so that QM212 protein is expressed. The culture was then maintained at 42C. for about 30 minutes to allow expression of QM212 to occur and form a QM212-containing culture having about 75 to 150 milligrams (mg) QM212 per 400 mls of culture.

The QM212-containing culture (400 mls) was centrifuged at 10,000 rpm in a JAQ-10 Sorval rotor (Beckman Instruments, Fullerton Calif.) for 10 minutes to form a cell pellet. The cell pellet was retained and resuspended in lysis buffer [50 millimolar (mM) Tris-HCl, 1 mM EDTA, 0.1 mM PMSF, pH 8.0] at 4C. and a concentration of 10 mls per ml of cell pellet volume. The resuspended cell pellet was passed through a french press homogenizer (Matt-Guzlin) at 4C. three times to form a lysed bacterial cell suspension, and thereafter the suspension was centrifuged at 23,400× g for 45 minutes at 6C. to form a pellet. The pellet was resuspended in one-half the volume of lysis buffer used before the french press homogenization, and re-centrifuged at 23,400× g for 45 minutes at 6C. to form a washed pellet. The washed pellet was recovered and washed an additional two times with lysis buffer, resuspended and centrifuged procedure to form thrice-washed pellet.

The above thrice-washed pellet was resuspended in freshly prepared Gu-HCl buffer (6M guanidine-HCl, 50 mM Tris-HCl, 10 mM CaCl2, 100 mM KCl, 0.1 mM PMSF, pH 8.0) at 4C. and a concentration of about 9 mls per ml of thrice-washed pellet volume, and the suspension was thoroughly mixed to from a solubilized suspension. Thereafter, the solubilized suspension was centrifuged at 23,400× g for 30 minutes at 6C. and the resulting supernatant was recovered. The absorption at 280 nm (A280) of the recovered supernatant was then measured and additional Gu-HCl buffer was added to adjust the A280 to about 25 units, relative to Gu-HCl buffer alone having an A280 of 0.0 units, to form solubilized QM212 protein extract.

The solubilized QM212 protein extract containing guanidine-denatured QM212 protein was then treated as follows to allow the denatured QM212 protein to refold into a three dimensional "folded" conformation. Refolding buffer (50 mM Tris-HCl, 10 mM CaCl2, 50 mM KCl, pH 8.0) was prepared and precooled to about 4–7C., PMSF was added to 0.1 mM and immediately thereafter the refolding buffer containing PMSF was admixed with solubilized QM212 protein extract to a ratio of extract to buffer of about 1:200 to 1:500 to form a refolding admixture. The refolding admixture was maintained at about 4C. for 12 to 16 hours to form a refolded QM212-containing solution.

About 1600 mls of refolded QM212-containing solution was reduced in volume using an Amicon ultrafiltration unit fitted with a Pharmacia Ortega 0.3 micron ultrafilter having a 10,000 molecular weight cut off to a final volume of about 10 to 50 mls, and the reduced volume was dialyzed against 10 mM sodium phosphate buffer, pH 6.0 at 4C. using four changes of about 20 volume of dialysis buffer. The resulting dialysis and concentrated solution was applied to a MonoS cation exchange column (HR1010, Pharmacia, Piscataway, N.J.) pre-equilibrated with equilibration buffer of 10 mM phosphate buffer, pH 8.0. The column was then washed with the equilibrating buffer. A single peak, containing QM212 protein, was eluted using a linear gradient buffer ranging from 10 mM phosphate, pH 8.0 to 150 mM NaCl and the peak fraction was collected. The collected peak fraction was then extensively dialyzed by 5 successive dialyses of 500 mls each at 4C. against 1 mM EDTA to remove any metal ions that may have been present. The EDTA dialysis was followed by extensive dialysis in metal free phosphate buffer to remove EDTA, to form a metal-free QM212 protein solution. The isolated QM212 protein is capable of forming a coordination complex with a metal ion and is comprised of an amino acid sequence that defines a variable domain of an immunoglobulin and three contact amino acid residues in that variable domain that define a metal binding site.

The metal-free QM212 protein solution, as analyzed on SDS-PAGE using a 20 percent polyacrylamide gel, displayed a single homogenous band with an electrophoretic mobility of about 26,500 daltons. Thus, the metal-free QM212 protein solution is a homogeneous composition containing the metal binding molecule QM212.

The related protein 4-4-20/212 was also prepared by the above procedures for use as a control in studies described below. 4-4-20/212 protein was expressed from an expression vector provided by Dr. Syd Johnson (Genex Corp., Md.) that differs from pQM212 only in the substitutions described in Example 1a.

2. Metal Binding Assay

Metal binding to a protein was measured by the quenching of fluorescence of tryptophan residues present in the protein in the presence or absence of added metal ions. A solution containing metal-free QM212 or 4-4-20/212 protein, prepared as in Example 1b, was diluted in 15 mM sodium phosphate, pH 6.0 to a concentration of 150 nanomolar (nM), using a molecular weight of about 26,500 daltons for each protein to calculate molarity, to form a quenching admixture. Fluorescence was determined in the quenching admixture using a RF500-U spectrofluorophotometer (Shimadzu, Japan) using an excitation wavelength of 292 nm, and then detecting an emission spectrum using a band width of 5 nm for both excitation and emission. Emission was detected at 343 nm when measuring fluorescence of a QM212-containing solution, and was detected at 352 nm when measuring a 4-4-20/212-containing solutions because these wavelengths were determined to represent the emission maximum for each protein when emission spectrums were measured over a 300 to 450 nm range. Fluorescence was measured in a 1 ml solution, with varying amounts of copper (II) chloride [Cu(II)] added in the range of 0 to 30 micromolar (µM) to the quenching admixture before excitation and emission measurements were conducted. Fluorescence quenching is expressed as a ratio F/Fo, where 1.0 is an arbitrary unit of 0% quenching in a solution having no added metal (Fo) and F is the emission measured when metal is added.

FIG. 3 shows that Cu(II) quenched fluorescence of the tryptophan residues present in the QM212 protein solution. In contrast, Cu(II) did not substantially quench fluorescence associated with 4-4-20/212 protein. The data also shows that Cu(II) fluorescence quenching of QM212 displays saturation behavior above about 12–15 mM Cu(II) with an apparent binding constant of $2 \times 10^5 M^{-1}$.

The three dimensional structure of the present antibody (4T4-20) with bound fluorescein is known (Herron et al., Proteins, 5:271–286, 1989), and five of the six tryptophan residues in both QM212 and the parent antibody are in close proximity to both the antigen combining site and the metal binding site produced by the present invention. Based on proximity, it was anticipated and subsequently shown by the above quenching data that bound metal ions efficiently quenched tryptophan fluorescence in a manner analogous to that shown in studies on model metalloprotein systems demonstrating Cu(II) to be a particularly effective quencher of tryptophan in the region of metal binding, followed by nickel as Ni(II) and cobalt as Co(II). The efficient nature of the quenching with QM212 by Cu(II) indicates that the Cu(II) atom is relatively near most of the tryptophan residues, an observation consistent with the occurrence of binding in the metal binding sites of QM212. Thus, the quenching results from a specific metal protein binding interaction, indicating that QM212 specifically binds metal, i.e., that QM212 is a metal binding protein capable of forming a coordination complex with a metal cation, whereas 4-4-20/212 does not specifically bind metal.

In a related experiment, EDTA, in molar excess of the amount of Cu(II) present, was added to the quenching admixture, and the emission was measured. Excess EDTA returned the level of fluorescence intensity back up to the level of the QM212 protein when measured with no added Cu(II). These data indicate that quenching is the result of a conventional reversible metal protein interaction found in metalloproteins and not the result of irreversible changes in tryptophan caused by contact with metal ions.

The ability of the metal binding protein, QM212, to bind other metal cations was measured as inhibition of Cu(II) binding to QM212 by competing ions, zinc as Zn(II) and cadmium as Cd(II). Prior to adding Cu(II) to the quenching admixture described above, 100 mM Zn(II) or 500 uM Cd(II) was added, and the fluorescence quenching was measured as above. FIGS. 4A and 4B, respectively, show that both zinc and cadmium bind QM212 in a dose dependent manner sufficiently to inhibit Cu(II) binding to QM212. Thus, many metal ions, including Cu(II), Zn(II), Cd(II), Ni(II) and Co(II), that present ligands to form tetrahedral coordination complex, including Cu(II), Zn(II), Cd(II), Ni(II) and Co(II) can bind to the metal binding protein of the present invention.

3. Antigen Binding Assay

Because QM212 as a model metalloantibody is derived from a light chain portion of an anti-fluorescein monoclonal antibody, the ability of QM212 to immunoreact with antigen could be determined using fluorescein. The binding of fluorescein to QM212 was measured by detecting the fluorescence quenching effect of QM212 on the excitation spectrum of fluorescein. See for example, J. N. Herron in *Fluorescein Hapten: An Immunological Probe*, E. W. Voss, Jr., Ed. CRC Press, Boca Raton, Fla. 1984 pp 49–76. The excitation spectrum of a solution containing 15 mM sodium phosphate, pH 6.0, and 7.0 nm fluorescein (spectrometry standard grade) was measured in the presence of various amount of QM212 prepared as in Example 1b using a spectrofluorophotometer (Shimadzu). Excitation at 400 to 520 nm was followed by measuring emission at 530 nm using a 5 nm band width for both excitation and emission. The excitation spectra data in FIGS. 5 and 6 is expressed as fluorescence intensity following excitation at 400 to 520 nm.

The excitation spectrum data resulting from the admixture of QM212 with fluorescein in amounts ranging from 0 to 7.7 uM is shown in FIG. 5. As more QM212 was added to the fluorescein solution, the amount of excitation was reduced, quenching the excitation of the fluorescein by about 80 percent (maxima to maxima). The excitation maxima shifted from about 493 nm to about 507 nm as QM212 bound fluorescein. A similar result was observed when 4-4-20/212 protein was used in place of QM212. These data indicate that fluorescein binds QM212 in a manner similar to fluorescein binding to 4-4-20/212, the latter of which has been characterized as an antigen antibody immunoreaction. Bird et al., *Science*, 242:423–426, 1988. Thus, QM212 has properties of an antibody molecule and therefore is an example of a metal binding antibody molecule.

To establish that QM212 can simultaneously bind both a metal and an antigen, and function as a metalloantibody, the effect of metal on the fluorescein excitation spectrum was measured when the fluorescein was bound to QM212. Solutions were prepared containing 15 nM sodium phosphate, pH 6.0, 7.0 nM of fluorescein and 7.7 uM QM212. Thereafter, various amount of Cu(II) were added to each solution ranging form 0 to 30 uM, and the excitation spectra measured. The data are shown in FIG. 6.

With no added Cu(II), similar to the condition shown in FIG. 5 when fluorescein was fully bound by QM212, the spectrum had a peak intensity of about 21.60 at the maxima of about 508 nm. With added Cu(II), the quenching was not reversed as would be expected if fluorescein was displaced by Cu(II) binding to QM212. Rather, the excitation spectrum maxima shifted from about 508 nm to about 494 nm and decreased as more Cu(II) was added. Saturation was observed to occur at about 18 uM Cu(II). No additional changes in spectrum were seen with 18 to 21 uM Cu(II). As expected, no Cu(II)-dependent perturbation of bound fluorescein fluorescence was seen when the above experiment was conducted using 4-4-20/212 protein in place of the QM212 protein.

These data indicate that the QM212 molecule can simultaneously bind Cu(II) and fluorescein on the QM212 molecule. The perturbed nature of the fluorescein excitation maxima observed as Cu(II) was added indicates that the metal cation, Cu(II), was bound in close proximity to the fluorescein, thus showing that the Cu(II) atom is binding in the metal binding site that was engineered by the present invention to be located closely adjacent to the antigen binding site.

4. Identification of the Immunoglobulin Variable Domain Sites for Introducing a Metal Ligand The structure of antibody variable domains of HyHEL5, HyHEL10, Newm, J539, HEd10, and Kol, available from the Protein Data Bank described by Bernstein et al., *J. Mol. Biol.*, 112:535–542 (1977), and D1.3, described by Amit et al., *Science*, 233:747–753 (1986) and supplied by Roberto Poljak, were compared by superimposing individual light chain variable ($V_L$) and heavy chain variable ($V_H$) domains onto the corresponding domains of McPC603 described by Bernstein et al., *J. Mol. Biol.*, 112:535–542 (1977). A slightly modified set of the common B-sheet framework residues of Chothia et al., *J. Mol. Biol.*, 196:901–917 (1987), was used to define the one-to-one correspondence of the superposition. In the numbering scheme of Kabat et al., in *Sequences of Proteins of Immunological Interest*, 4th Ed., U.S. Department of Health and Human Services, National Institute of Health, Bethesda, Md. (1987), correspondences defined herein are the $V_L$ residues 4–6, 9, 11–13, 19–25, 33–49, 53–55, 61–76, 84–90, and 97–107, and the $V_H$ residues 3–12, 17–25, 33–52, 56–60, 68–82, 88–95, and 102–112. $V_L$ 10 and 106A were excluded because these residues are deleted in some sequences. The coordinates for the crystallographic structure of the anti-fluorescein antibody 4-4-20 were made available by Edmundson et al., *Proteins*, 5:271–280 (1989). A search of the Protein Data Bank provided crystallographic structures of five catalytic zinc-containing proteins: carbonic anhydrase, by Kannan et al., *Proc. Natl. Acad. Sci. USA*, 75:51–55 (1975); carboxypeptidase A, by Rees et al., *J. Mol. Biol.*, 168:367–387 (1983); superoxide dismutase by Tainer et al., *Nature*, 306:284–287 (1983); alcohol dehydrogenase, by Branden et al., in *Enzymes*, ed. Boyer, P. D. (Academic Press, New York), 3rd edition); and thermolysin, by Holmes et al., *J. Mol. Biol.*, 160:623–939 (1982).

Superpositions of the eight sets of antibody light and heavy chain variable domains ($V_L$ and $V_H$, respectively) identified structurally conserved sites within the sequence-variable complementarity determining regions (CDRs). The pattern for catalytic zinc sites included two ligands close in sequence, a sequence-distant ligand, and a main-chain hydrogen bond joining two ligands. In both $V_L$ and $V_H$, the stereochemistry of five structurally conserved sites general to all known antibody structures matched that of the zinc ligands of carbonic anhydrase (CAB): three residues on two hydrogen-bonded antiparallel β-strands.

The CDRs of the antibodies were examined for all main-chain hydrogen bonds, defined by a maximum distance of 3.5 Å between nitrogen and oxygen atoms. The program INSIGHT (from Biosym Technologies, Inc.) was used to superimpose the $C_\alpha$ and $C_\beta$ atoms of zinc ligands onto the antibody CDRs, to examine and analyze the superimposed antibody structures, and to create FIGS. 7A and 7B.

Superposition of the $V_L$ and $V_H$ framework of seven antibodies onto the McPC603 antibody described by Getzoff et al., *Adv. Immunol.*, 43:1–98 (1988), revealed that the conserved β-sheet structure of the framework region was continued into the CDRs in all the antibody structures. These CDR regions had the characteristics required for a general cofactor site—conserved predictable structure with allowed sequence variability, so that mutations can be introduced without perturbing the overall structure. The first CDR of $V_L$ (L1) is a Greek key loop joining non-adjacent β-strands across the end of the β-barrel, L2 is an extended strand and β-turn (except in Newm), and L3 is a continuation of two adjacent framework β-strands with a variable connecting loop. In $V_H$, H1 is an extended β-strand, H2 is two adjacent β-strands connected with a variable loop, and H3 is a continuation of two β-strands with a highly variable connecting loop. Regions of the L1, L3, H2, and H3 CDRs described herein showed the most conformational variability and therefore provide the most preferable sites for introducing a metal binding site.

A search of crystallographic structures in the Protein Data Bank described by Bernstein et al., *J. Mol. Biol.*, 112:535–542 (1977) revealed several catalytic zinc-binding motifs. Three residues, predominantly histidine, but also glutamate, aspartate, and cysteine, coordinated the metal ion in a roughly tetrahedral geometry. Generally at least two of the ligands in zinc-binding proteins were close together in the protein sequence. An additional important structural characteristic of a metal-binding site not shown by sequence analysis is the presence of main-chain hydrogen bonds connecting two of the amino acid contact residues that provide a metal ligand.

The metal ligand stereochemistry of a metal-containing protein can include three secondary structure motifs with hydrogen-bonded main chains, namely adjacent β-strands, β-turns, and α-helices. The zinc ligands of carbonic anhydrase (CAB) described by Kannan et al., *Proc. Natl. Acad. Sci USA*, 72:51–55 (1975), representing the β-strand motif, were three of four residues in two adjacent hydrogen-bonded pairs joining two antiparallel β-strands. The two ligands on one β-strand were separated by one intervening residue. All four of the residues in the two adjacent hydrogen-bond pairs had their $C\alpha$–$C_\beta$ bonds pointing towards the zinc ion and the open coordination position, so predetermined substitution of any three of the four side chains creates a metal-binding site. In carboxypeptidase A described by Rees et al., *J. Mol. Biol.*, 168:367–387 (1983), and superoxide dismutase described by Tainer et al., *Nature*, 306:284–287 (1983), two of the zinc ligands, separated by two intervening residues, were in the 1 and 4 positions of a type I β-turn. In the α-helical motif seen in thermolysin described by Holmes et al., *J. Mol. Biol.*, 160:623–639 (1982), elastase described by Thayer, in his Ph.D. thesis, University of Colorado (1989), and neutral protease described by Pauptit et al., *J. Mol. Biol.*, 199:525–537 (1988), two histidine ligands, separated by three intervening residues, were linked by an α-helical, main-chain hydrogen bond. The third ligand was on an adjacent antiparallel helix.

The main-chain hydrogen-bonding constraint in all of the above enzyme structures caused two of the ligating side chains to extend away from the backbone in approximately the same direction, positioning the zinc-ligating atoms near to each other. Only alcohol dehydrogenase, described by Branden et al., in *Enzymes*, ed. Boyer, P. D. Academic Press, New York, 3rd editions which differs from the other catalytic sites both in ligand type and in the sequential spacing described by Valee et al., *Proc. Natl. Acad. Sci. USA*, 87:220–224 (1990), contained a catalytic zinc site lacking two hydrogen-bonded ligands. Thus, the available protein structures with catalytic zinc sites showed that a main-chain hydrogen bond was important for proper ligand arrangement, whereas the major backbone conformation, β-sheet, β-turn, or α-helix, was variable. Therefore, the CDRs of the available antibody structures were examined for main-chain hydrogen-bonded residues that would make up two of the three metal ligands (contact amino acid residues). The metalloenzyme zinc-binding sites were then superimposed onto the identified antibody sites to provide three-dimensional templates for metal binding sites in antibodies.

Within the $V_L$ and $V_H$ CDRs so analyzed, 11 sites for metal coordination were identified, which together involve all six CDRs. The 11 sites are summarized in Table 1. Only one example each of hydrogen-bonded ligands with βturn or α-helical secondary structures was found. A general β-turn site on L2 placed the zinc ion between L2 and H3. A short helix in V lambda L1 should accommodate the zinc-binding site, placing an open coordination site for a water molecule between L1 and L3. However, the β-strand motif in CAB provided the best template for building general metalloantibody sites because it mimicked conserved structural features of the CDRs deep in the antibody binding pocket. For the eight antibodies examined, the CDRs, which consist of about 50 to 60 residues per antibody, contained nine general sites with stereochemistry similar to CAB. Five of these sites included the important hydrogen-bonding features: two placed the zinc in the center of the binding pocket (the L1–L3 site and the H1–H3 site), one placed the zinc between L1 and L3 (a L3 site), and two placed the zinc between H2 and L3 (the two H2 sites).

TABLE 1

Metal Binding Sites in Antibody CDRs

| Metal Binding Site[1] | Cation location[2] | H-Bond[3] | Other ligands |
|---|---|---|---|
| β-Strand | | | |
| L1 (34), L3 (89, 91) | Center | 34–89 | L1 (32) |
| L3 (90, 92, 97) | L1 and L3 | 90–97 | L3 (95) |
| L3 (89, 91, 96) | Center | 91:96 | |
| H1 (33, 35), H3 (95) | Center | 33–95 | |
| H1 (33, 35), H2 (50) | Center | 35:50 | H2 (52) |
| H1 (31, 33), H2 (52) | Center | 33:52 | |
| H2 (50, 52, 58) | H2 and L3 | 50–58 | H2 (56) |
| H2 (50, 58, 60) | H2 and L3 | 50–58 | |
| H3 (95, 101x, 101x-2)[4] | Center | 95:101x | |
| β-Turn | | | |
| L2 (50, 53, 55) | L2 and H3 | 50 . . . 53 | |
| α-Helix | | | |
| L1 (27d, 29), L3 (93)[5] | Above site | 27d . . . 29 | |

1. Numbering in parenthesis is for the amino acid residue position for a contact amino acid residue that contributes to a metal binding site. The numbers refer to the Kabat position number. The CDR in which the contact residue is located is also indicated.
2. The cation was either positioned in the center of the binding pocket between L3 and H3 (center), or between the two CDRs indicated.
3. Pairs of residues having hydrogen bonds conserved in all antibodies are indicated by 37 —" and those having N—O distances greater than 3.5 Å in some antibodies by " . . . ". Nonhydrogen-bonded pairs of residues that occur in β-strands are indicated by ":".
4. "101x" indicates either residue 101 or the preceding residue of H3, and "101x-2" indicates the residue located two amino acid residue positions away from 101x towards the amino terminus of the heavy chain, as described further herein.
5. The site is found in V lambda only. The amino acid residue position 27d in CDR L1 is located four amino acid residue positions away from position 29 towards the amino terminus of the light chain as described further herein.

For one such general site, an antibody model replacing position 34 on the first CDR of the light chain (L1) and positions 89 and 91 on L3 with histidine contact amino acid residues (ligands) formed a metal-binding site with an open coordination position at the bottom of the antibody binding pocket. For the anti-fluorescein antibody 4-4-20, modified as described in Examples 1–3, this L1–L3 site placed the zinc ion about 4 Å from the bound fluorescein, an indicator for metal binding.

The L1–L3 site satisfied all of the design requirements described herein: 1) a structurally conserved, sequence-variable region common to all antibodies, 2) a pair of hydrogen-bonded residues, and 3) three ligands that would position the metal and its solvent-exposed site to interact with bound antigen. The main-chain hydrogen bond between residue 34, the last residue of L1, and 89, the first residue of L3, continued the framework antiparallel β-sheet structure into the CDRs. The main-chain and side-chain positions in the L1–L3 site strongly resembles the zinc-binding site of CAB as shown in FIG. 7A. In all antibodies, the $C_\alpha$ and $C_\beta$ atoms of residue 89, 91 and 34 extended out from one side of the β-sheet with stereochemistry similar to residues 94, 96, and 119 of the enzyme CAB. In the antibody HyHEL5 shown in FIG. 7A, and similarly in the antibodies D13, HyHEL10, J539 and McPC603, the β-structure extended further up L1 and L3, providing a second hydrogen-bonded pair between residues 32 and 91, further mimicking CAB. Although the side chain of L1 residue 32 pointed up out of the antibody binding site rather than into it, the energy gained by metal binding is sufficient to position residue 32 as a metal ligand. Thus, the conserved structural pattern of the L1–L3 site seen in all antibody structures indicates that replacement of any three of residues 32, 34, 89, and 91 by histidines creates a metal-binding site in the antibody binding pocket. Superposition of zinc-ligating residues His 94, 96, and 119 of CAB described by Kannan et al., Proc. Natl. Acad. Sci. USA, 72:51–55 (1975), onto residues Gln 89, Trp 91, and Tyr 34 of the antibody HyHEL5, described by Sheriff et al., Proc. Natl. Acad. Sci. USA, 84:8075–8079 (1987), revealed that the zinc ion would be positioned near the center of the bottom of the binding pocket in an orientation to act as a catalytic cofactor as shown in FIG. 7A. Residue replacement and metal binding does not have a significant effect on the folding of the CDRs, because amino acid substitutions are not uncommon for these four antibody residue positions. For example, Tyr 34 is replaced by a histidine in both the antibodies J539 and HyHEL10.

A $V_L$ metal binding site positioned deep in the pocket, such as the L1–L3 site, interacts with a substrate whose binding site is formed by other antibody residues, especially those from the highly variable H3 shown in FIG. 7B. Because of H3 variability and its involvement in many antigen-antibody interactions as summarized by Amit et al., Science, 233:747–753 (1986); and Herron et al., Proteins, 5:271–280 (1989), chimeric antibodies composed of substrate-specific heavy chains and a metal-binding light chain are particularly preferred where the objective is to bind substrate adjacent to the metal ion as to facilitate catalysis.

5. Catalytic Antibody Design

The catalytic and binding sites of enzymes are usually well-conserved, while the binding sites of antibodies, made up of the CDRs, are inherently variable. Examination of the structures of catalytic zinc ion sites in proteins indicated a highly conserved stereochemistry including a specific main-chain hydrogen bond between two of the three ligands. Examination of antibody structures showed that regions of the CDRs have highly variable conformations determined by sequence and environment. Both metal and antigen binding may induce conformational rearrangements of these regions. See, for example Getzoff et al., *Science*, 235:1191–1196 (1987); and Getzoff et al., *Adv. Immunol.*, 43:1–98 (1988). However, the structurally conserved, but sequence variable, regions of the CDRs that are identified herein tolerate mutation without significant conformational perturbation.

Knowledge of the primary amino acid sequence of antibody CDRs is sufficient to construct metal-binding antibodies in a single design step using the methods described herein. Thus, the present teachings provide a general approach for remodeling antibody variable regions, specifically in the CDRs, to produce predetermined metal binding sites.

The ability to design metal binding sites in structurally conserved areas of the CDRs has broad implications for catalytic antibody design. For example, the humanized monoclonal antibodies described by Riechmann et al., *Nature*, 332:323–327 (1988) that are directed against medically important targets can be modified the present teachings while retaining binding, to achieve peptide bond cleavage or other chemical reactions. The ability to construct zinc coordination sites in antibodies shown here and to raise antipeptide antibodies that cross-react with flexible, exposed regions of proteins shown previously by Tainer et al., *Nature*, 312:127–133 (1984), suggests that sequence specific, site-directed proteases can be obtained by adding a zinc-binding site to the appropriate antibody. Also, combining metal-binding light chains prepared by the present methods with various heavy chain libraries raised to different substrates using the combinatorial repertoire methods of Sastry et al., *Proc. Natl. Acad. Sci. USA*, 86:5728–5732 (1989), Huse et al., *Science*, 246:1275–1281 (1989), and Ward et al., *Nature*, 341:544 (1989), extends this method to a wide variety of important reactions that use a metal cofactor.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. An isolated protein which forms a coordination complex with a metal cation, comprising:
   (a) a sequence of amino acid residues that includes a variable domain of an immunoglobulin, wherein said variable domain is a light chain variable domain having an L3 region; and
   (b) three contact amino acid residues in said variable domain that define a metal binding site, wherein said three contact amino acid residues are located at any three of the four Kabat amino acid residue position numbers 90, 92, 95 and 97.

2. An isolated protein which forms a coordination complex with a metal cation, comprising:
   (a) a sequence of amino acid residues that includes a variable domain of an immunoglobulin, wherein said variable domain is a light chain variable domain having an L3 region; and
   (b) three contact amino acid residues in said variable domain that define a metal binding site, wherein said three contact amino acid residues are located at Kabat amino acid residue position numbers 89, 91 and 96.

3. An isolated protein which forms a coordination complex with a metal cation, comprising:
   (a) a sequence of amino acid residues that includes a variable domain of an immunoglobulin, wherein said variable domain is a heavy chain variable domain having an H1 region and an H2 region; and
   (b) three contact amino acid residues in said variable domain that define a metal binding site, wherein said three contact amino acid residues are located at Kabat amino acid residue position numbers 31, 33 and 52.

4. An isolated protein which forms a coordination complex with a metal cation, comprising:
   (a) a sequence of amino acid residues that includes a variable domain of an immunoglobulin, wherein said variable domain is a heavy chain variable domain having an H2 region; and
   (b) three contact amino acid residues in said variable domain that define a metal binding site, wherein said three contact amino acid residues are located at any three of the four Kabat amino acid residue position numbers 50, 52, 56 and 58.

5. An isolated protein which forms a coordination complex with a metal cation, comprising:
   (a) a sequence of amino acid residues that includes a variable domain of an immunoglobulin, wherein said variable domain is a heavy chain variable domain having an H2 region; and
   (b) three contact amino acid residues in said variable domain that define a metal binding site, wherein said three contact amino acid residues are located at Kabat amino acid residue position numbers 50, 58 and 60.

6. An isolated protein which forms a coordination complex with a metal cation, comprising:
   (a) a sequence of amino acid residues that includes a variable domain of an immunoglobulin, wherein said variable domain is a heavy chain variable domain having an H3 region; and
   (b) three contact amino acid residues in said variable domain that define a metal binding site, wherein said three contact amino acid residues are located at Kabat amino acid residue position numbers 95, 101x and 101x-2.

7. A modified, isolated protein which forms a coordination complex with a metal cation, comprising:
   (a) a sequence of amino acid residues that includes a variable domain of an immunoglobulin; and
   (b) three contact amino acid residues in said variable domain that define a metal binding site, wherein said contact amino acid residues are selected from the group of contact amino acid residues consisting of histidine, aspartic acid, cysteine and glutamic acid.

8. The protein of claim 7, wherein said three contact amino acid residues are histidine.

9. An isolated protein which forms a coordination complex with a metal cation, comprising:
   (a) a sequence of amino acid residues that includes a variable domain of an immunoglobulin; and
   (b) three contact amino acid residues in said variable domain that define a metal binding site, wherein said three contact amino acid residues are two histidines and an amino acid residue selected from the group consisting of histidine, glutamic acid, aspartic acid and cysteine.

10. An isolated protein which forms a coordination complex with a metal cation, comprising a sequence of amino acid residues that includes a variable domain of an immunoglobulin and three contact amino acid residues in said variable domain that define a metal binding site, wherein said metal cation is complexed with said protein through tetrahedral coordinated contacts provided by said contact amino acid residues, and wherein said metal cation is selected from the group consisting of Cu(II), Zn(II), Ni(II), Co(II) and Cd(II).

11. The protein of claim 10, wherein said metal cation is Cu(II).

12. A modified, isolated protein which forms a coordination complex with a metal cation, comprising:

(a) a sequence of amino acid residues that includes a variable domain of an immunoglobulin; and (b) three contact amino acid residues in said variable domain that define a metal binding site, wherein said protein is an immunoglobulin.

13. The protein of claim 12, wherein said immunoglobulin is an antibody.

14. The protein of claim 13, wherein said antibody is a heterodimeric antibody molecule comprised of two immunoglobulin heavy chain molecules and two immunoglobulin light chain molecules.

15. The protein of claim 13, wherein said antibody is a single-chain antibody.

16. The protein of claim 13, wherein said antibody is a catalytic antibody molecule which promotes a predetermined chemical reaction.

17. An immunoglobulin which forms a coordination complex with a metal cation, comprising an immunoglobulin light chain variable domain having an L1 region and an L3 region, wherein said light chain variable domain includes three contact amino acid residues forming a metal binding site, and wherein:

(a) said contact amino acid residues are selected from the group consisting of histidine, aspartic acid, cysteine and glutamic acid; and (b) said contact amino acid residues are located at any three of the four Kabat amino acid residue position numbers 32, 34, 89, and 91 in said variable domain.

18. A modified immunoglobulin molecule which forms a coordination complex with a metal cation, comprising:

(a) a sequence of amino acid residues that includes a variable domain of an immunoglobulin; and (b) three contact amino acid residues in said variable domain that define a metal binding site.

19. The molecule of claim 18, wherein said variable domain is a light chain variable domain having an L1 region and an L3 region, and said three contact amino acid residues are located at any three of the four Kabat amino acid residue position numbers 32, 34, 89, and 91.

20. The molecule of claim 18, wherein said variable domain is a light chain variable domain having an L2 region and said three contact amino acid residues are located at Kabat amino acid residue position numbers 50, 53 and 55.

21. The molecule of claim 18, wherein said variable domain is a light chain variable domain having an L1 region and an L3 region, and said three contact amino acid residues are located at Kabat amino acid residue position numbers 27d, 29 and 93.

22. The molecule of claim 18, wherein said variable domain is a heavy chain variable domain having an H1 and an H3 region, and said three contact amino acid residues are located at Kabat amino acid residue position numbers 33, 35 and 95.

23. The molecule of claim 18, wherein said variable domain is a heavy chain variable domain having an H1 region and an H2 region, and said three contact amino acid residues are located at any three of the four Kabat amino acid residue position numbers 33, 35, 50 and 52.

24. The molecule of claim 18, wherein said three contact amino acid residues are selected from the group of contact amino acid residues consisting of histidine, aspartic acid, cysteine and glutamic acid.

25. The molecule of claim 24, wherein said three contact amino acid residues are histidine.

26. The molecule of claim 18, further comprising a metal cation complexed with said protein through tetrahedral coordinated contacts provided by said contact amino acid residues.

27. The molecule of claim 26, wherein said metal cation is selected from the group consisting of Cu(II), Zn(II), Ni(II), Co(II) and Cd(II).

28. The molecule of claim 26, wherein said metal cation is Cu(II).

29. The molecule of claim 18, wherein said immunoglobulin molecule is an antibody.

30. The molecule of claim 29, wherein said antibody is a heterodimeric antibody molecule comprised of two immunoglobulin heavy chain molecules and two immunoglobulin light chain molecules.

31. The molecule of claim 29, wherein said antibody is a single-chain antibody.

32. The molecule of claim 29, wherein said antibody is a catalytic antibody molecule which promotes a predetermined chemical reaction.

* * * * *